(12) United States Patent
Ouchi et al.

(10) Patent No.: US 11,306,358 B2
(45) Date of Patent: Apr. 19, 2022

(54) METHOD FOR DETERMINING GENETIC CONDITION OF FETUS

(71) Applicant: FUJIFILM Corporation, Tokyo (JP)

(72) Inventors: Aya Ouchi, Ashigara-kami-gun (JP); Takayuki Tsujimoto, Ashigara-kami-gun (JP); Masaya Nagase, Ashigara-kami-gun (JP); Yasuyuki Ishii, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 818 days.

(21) Appl. No.: 15/712,785

(22) Filed: Sep. 22, 2017

(65) Prior Publication Data
US 2018/0087112 A1   Mar. 29, 2018

Related U.S. Application Data

(63) Continuation of application No. PCT/JP2016/060444, filed on Mar. 30, 2016.

(30) Foreign Application Priority Data

Mar. 31, 2015 (JP) .............................. JP2015-074318

(51) Int. Cl.
| | | |
|---|---|---|
| *C12Q 1/68* | (2018.01) | |
| *C12Q 1/6883* | (2018.01) | |
| *C12Q 1/6811* | (2018.01) | |
| *C12Q 1/6876* | (2018.01) | |
| *C12N 15/10* | (2006.01) | |
| *C12N 15/09* | (2006.01) | |

(52) U.S. Cl.
CPC ....... *C12Q 1/6883* (2013.01); *C12N 15/1089* (2013.01); *C12Q 1/6811* (2013.01); *C12Q 1/6876* (2013.01); *C12N 15/09* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2009/0275025 A1 | 11/2009 | Rihet et al. |
| 2010/0070452 A1 | 3/2010 | Nakamura |
| 2013/0072402 A1 | 3/2013 | Takamura et al. |
| 2013/0103368 A1 | 4/2013 | Farmer et al. |
| 2013/0123120 A1 | 5/2013 | Zimmermann et al. |
| 2013/0196862 A1* | 8/2013 | Rabinowitz ............ G16B 20/00 506/2 |

FOREIGN PATENT DOCUMENTS

| | | |
|---|---|---|
| JP | 2009-533030 A | 9/2009 |
| JP | 2011-62085 A | 3/2011 |
| WO | WO 03/074723 A2 | 9/2003 |
| WO | WO 2008/004691 A1 | 1/2008 |
| WO | WO 2012/023298 A1 | 2/2012 |
| WO | WO 2012/108920 A1 | 8/2012 |
| WO | WO 2014/036743 A1 | 3/2014 |
| WO | WO 2017/145738 A1 | 8/2017 |
| WO | WO 2017/145739 A1 | 8/2017 |

OTHER PUBLICATIONS

Zhang et al. (PLoS One 2013, 8(1):e5436, p. 1-9) (Year: 2013).*
Chuang et al. (BMC Research Notes, 2012, 5:306) (Year: 2012).*
Haas et al. (Genome Research, 2011, 21:494-504) (Year: 2011).*
Kinde et al. (PLoS One, 2012, vol. 7, No. 7, e41162, p. 1-8) (Year: 2012).*
Chuang et al., "URPD: a specific product primer design tool," BMC Research Notes, BioMed Central Ltd., GB, vol. 5, No. 1, Jun. 19, 2012, XP021122796, pp. 1-9.
European Communication pursuant to Article 94(3) EPC for corresponding European Application No. 16772992.0, dated Nov. 28, 2018.
Ye et al., "Primer-BLAST: A tool to design target-specific primers for polymerase chain reaction," BMC Bioinformatics, BioMed Central, London, GB, vol. 13, No. 1, Jun. 18, 2012, XP021132324, pp. 1-11.
Japanese Office Action, dated Jul. 17, 2018, for corresponding Japanese Application No. 2017-510122, with an English translation.
Béroud et al., "Prenatal diagnosis of spinal muscular atrophy by genetic analysis of circulating fetal cells," The Lancet, vol. 361, Mar. 22, 2003, pp. 1013-1014.
Extended European Search Report for Application No. 16772992.0, dated Feb. 14, 2018.
Huep et al., "An easy-to-use primer design tool to address paralogous loci and T-DNA insertion sites in the genome of *Arabidopsis thaliana*," Plant Methods, vol. 10, No. 28, 2014, pp. 1-10.

(Continued)

*Primary Examiner* — Stephanie K Mummert
(74) *Attorney, Agent, or Firm* — Birch, Stewart, Kolasch & Birch, LLP

(57) ABSTRACT

Provided is a method for determining a genetic condition of a fetus, the method including: an objective region selection step of selecting an objective region for determining the genetic condition, from regions on a human genome; a step of isolating a single cell from a maternal blood sample; a step of extracting genomic DNA from the single cell; a step of performing PCR amplification on the objective region using a primer set designed so as to perform the PCR amplification on the objective region using genomic DNA extracted from the single cell as a template; and a DNA sequencing step of decoding a DNA base sequence of a PCR amplification product of the objective region, in which the primer set designed so as to perform the PCR amplification on the objective region is designed through a method for designing a primer set used for the polymerase chain reaction, the method for designing a primer set including a first stage selection step based on a local alignment score and a second stage selection step based on a global alignment score.

12 Claims, 2 Drawing Sheets

Specification includes a Sequence Listing.

(56) References Cited

OTHER PUBLICATIONS

Hviid, "In-cell PCR method for specific genotyping of genomic DNA from one individual in a mixture of cells from two individuals: a model study with specific relevance to prenatal diagnosis based on fetal cells in maternal blood," Clinical Chemistry, vol. 48, No. 12, 2002, pp. 2115-2123.
Zhang et al., "A single cell level based method for copy number variation analysis by low coverage massively parallel sequencing," PloS one, vol. 8, Issue 1, e54236, Jan. 23, 2013, pp. 1-9.
International Search Report and Written Opinion of the International Searching Authority (Forms PCT/ISA/237 and PCT/ISA/210), dated Jul. 5, 2016, for International Application No. PCT/JP2016/060444, with an English translation.
Chinese Office Action and Search Report dated Mar. 19, 2020, for corresponding Chinese Patent Application No. 201680018965.0, with partial translation.

\* cited by examiner

FIG. 2

SEQUENCE LISTING

```
<160> NUMBER OF SEQ ID NOS: 57

<210> SEQ ID NO 1
<211> LENGTH: 37
<212> TYPE: DNA
<213> ORGANISM: Artificial Sequence
<220> FEATURE:
<223> OTHER INFORMATION: Synthetic; SNP id: rs7981616, chr13: 25264999

<400> SEQUENCE: 1
cgctcttccg atctctggct tggccttggg aatgtgg                              37

<210> SEQ ID NO 2
<211> LENGTH: 37
<212> TYPE: DNA
<213> ORGANISM: Artificial Sequence
<220> FEATURE:
<223> OTHER INFORMATION: Synthetic; SNP id: rs7981616, chr13: 25265178

<400> SEQUENCE: 2
cgctcttccg atctgacggc aatatggcca atgatgg                              37

<210> SEQ ID NO 3
<211> LENGTH: 37
<212> TYPE: DNA
<213> ORGANISM: Artificial Sequence
<220> FEATURE:
<223> OTHER INFORMATION: Synthetic; SNP id: rs1408184, chr13: 46946120

<400> SEQUENCE: 3
cgctcttccg atctctgctg tcagtctcag gatatgg                              37
```

```
<210> SEQ ID NO 4
<211> LENGTH: 37
<212> TYPE: DNA
<213> ORGANISM: Artificial Sequence
<220> FEATURE:
<223> OTHER INFORMATION: Synthetic; SNP id: rs1408184, chr13: 46946292

<400> SEQUENCE: 4
cgctcttccg atctgacgat accacagact ccgttgg                          37

<210> SEQ ID NO 5
<211> LENGTH: 37
<212> TYPE: DNA
<213> ORGANISM: Artificial Sequence
<220> FEATURE:
<223> OTHER INFORMATION: Synthetic; SNP id: rs1801244, chr13: 52544717

<400> SEQUENCE: 5
cgctcttccg atctctgact gctctggttg attgtgg                          37

<210> SEQ ID NO 6
<211> LENGTH: 37
<212> TYPE: DNA
<213> ORGANISM: Artificial Sequence
<220> FEATURE:
<223> OTHER INFORMATION: Synthetic; SNP id: rs1801244, chr13: 52544880

<400> SEQUENCE: 6
cgctcttccg atctgactgt tctactaacc ctcttgg                          37

<210> SEQ ID NO 7
<211> LENGTH: 37
<212> TYPE: DNA
<213> ORGANISM: Artificial Sequence
<220> FEATURE:
<223> OTHER INFORMATION: Synthetic; SNP id: rs2296984, chr13: 99457303

<400> SEQUENCE: 7
cgctcttccg atctctgttc ccggtctgcg taaatgg                          37

<210> SEQ ID NO 8
<211> LENGTH: 37
<212> TYPE: DNA
<213> ORGANISM: Artificial Sequence
<220> FEATURE:
<223> OTHER INFORMATION: Synthetic; SNP id: rs2296984, chr13: 99457464

<400> SEQUENCE: 8
cgctcttccg atctgacggt caaccctaag gatctgg                          37

<210> SEQ ID NO 9
<211> LENGTH: 37
<212> TYPE: DNA
<213> ORGANISM: Artificial Sequence
<220> FEATURE:
<223> OTHER INFORMATION: Synthetic; SNP id: rs946837, chr13: 101287239

<400> SEQUENCE: 9
cgctcttccg atctctgtca ttctgttcat cagctgg                          37

<210> SEQ ID NO 10
<211> LENGTH: 37
<212> TYPE: DNA
<213> ORGANISM: Artificial Sequence
<220> FEATURE:
<223> OTHER INFORMATION: Synthetic; SNP id: rs946837, chr13: 101287398
```

-continued

<400> SEQUENCE: 10
cgctcttccg atctgactaa cctgttcttc cgagtgg    37

<210> SEQ ID NO 11
<211> LENGTH: 37
<212> TYPE: DNA
<213> ORGANISM: Artificial Sequence
<220> FEATURE:
<223> OTHER INFORMATION: Synthetic; SNP id: rs2230233, chr18: 29104659

<400> SEQUENCE: 11
cgctcttccg atctctgttt gcagcttgaa gggatgg    37

<210> SEQ ID NO 12
<211> LENGTH: 37
<212> TYPE: DNA
<213> ORGANISM: Artificial Sequence
<220> FEATURE:
<223> OTHER INFORMATION: Synthetic; SNP id: rs2230233, chr18: 29104819

<400> SEQUENCE: 12
cgctcttccg atctgacgag catctgtttc tatgtgg    37

<210> SEQ ID NO 13
<211> LENGTH: 37
<212> TYPE: DNA
<213> ORGANISM: Artificial Sequence
<220> FEATURE:
<223> OTHER INFORMATION: Synthetic; SNP id: rs7233515, chr18: 44585836

<400> SEQUENCE: 13
cgctcttccg atctctgcat cggactttgc ttgatgg    37

<210> SEQ ID NO 14
<211> LENGTH: 37
<212> TYPE: DNA
<213> ORGANISM: Artificial Sequence
<220> FEATURE:
<223> OTHER INFORMATION: Synthetic; SNP id: rs7233515, chr18: 44585977

<400> SEQUENCE: 14
cgctcttccg atctgactat atgtaggccg aagttgg    37

<210> SEQ ID NO 15
<211> LENGTH: 37
<212> TYPE: DNA
<213> ORGANISM: Artificial Sequence
<220> FEATURE:
<223> OTHER INFORMATION: Synthetic; SNP id: rs4940019, chr18: 48333122

<400> SEQUENCE: 15
cgctcttccg atctctggtg acgctttta gcactgg    37

<210> SEQ ID NO 16
<211> LENGTH: 37
<212> TYPE: DNA
<213> ORGANISM: Artificial Sequence
<220> FEATURE:
<223> OTHER INFORMATION: Synthetic; SNP id: rs4940019, chr18: 48333301

<400> SEQUENCE: 16
cgctcttccg atctgactct ttagagggag agattgg    37

<210> SEQ ID NO 17
<211> LENGTH: 37

```
<212> TYPE: DNA
<213> ORGANISM: Artificial Sequence
<220> FEATURE:
<223> OTHER INFORMATION: Synthetic; SNP id: rs3809971, chr18: 56204947

<400> SEQUENCE: 17
cgctcttccg atctctgccc aacaagagaa tctatgg                              37

<210> SEQ ID NO 18
<211> LENGTH: 37
<212> TYPE: DNA
<213> ORGANISM: Artificial Sequence
<220> FEATURE:
<223> OTHER INFORMATION: Synthetic; SNP id: rs3809971, chr18: 56205121

<400> SEQUENCE: 18
cgctcttccg atctgactga cttcagggag cctgtgg                              37

<210> SEQ ID NO 19
<211> LENGTH: 37
<212> TYPE: DNA
<213> ORGANISM: Artificial Sequence
<220> FEATURE:
<223> OTHER INFORMATION: Synthetic; SNP id: rs3744877, chr18: 77894713

<400> SEQUENCE: 19
cgctcttccg atctctgtct ggggttcttc ctactgg                              37

<210> SEQ ID NO 20
<211> LENGTH: 37
<212> TYPE: DNA
<213> ORGANISM: Artificial Sequence
<220> FEATURE:
<223> OTHER INFORMATION: Synthetic; SNP id: rs3744877, chr18: 77894884

<400> SEQUENCE: 20
cgctcttccg atctgacctg aggaggagac tgtctgg                              37

<210> SEQ ID NO 21
<211> LENGTH: 37
<212> TYPE: DNA
<213> ORGANISM: Artificial Sequence
<220> FEATURE:
<223> OTHER INFORMATION: Synthetic; SNP id: rs2073370, chr21: 35260401

<400> SEQUENCE: 21
cgctcttccg atctctggcc tcgaagagag ggaatgg                              37

<210> SEQ ID NO 22
<211> LENGTH: 37
<212> TYPE: DNA
<213> ORGANISM: Artificial Sequence
<220> FEATURE:
<223> OTHER INFORMATION: Synthetic; SNP id: rs2073370, chr21: 35260571

<400> SEQUENCE: 22
cgctcttccg atctgacgac cacaatctct cccgtgg                              37

<210> SEQ ID NO 23
<211> LENGTH: 37
<212> TYPE: DNA
<213> ORGANISM: Artificial Sequence
<220> FEATURE:
<223> OTHER INFORMATION: Synthetic; SNP id: rs1041439, chr21: 40571215

<400> SEQUENCE: 23
```
cgctcttccg atctctgctg ggcagtgtga gaactgg                         37

<210> SEQ ID NO 24
<211> LENGTH: 37
<212> TYPE: DNA
<213> ORGANISM: Artificial Sequence
<220> FEATURE:
<223> OTHER INFORMATION: Synthetic; SNP id: rs1041439, chr21: 40571388

<400> SEQUENCE: 24
cgctcttccg atctgactct gaaagtgtct gttctgg                         37

<210> SEQ ID NO 25
<211> LENGTH: 37
<212> TYPE: DNA
<213> ORGANISM: Artificial Sequence
<220> FEATURE:
<223> OTHER INFORMATION: Synthetic; SNP id: rs3746887, chr21: 41032678

<400> SEQUENCE: 25
cgctcttccg atctctgctc atcccacaaa cagttgg                         37

<210> SEQ ID NO 26
<211> LENGTH: 37
<212> TYPE: DNA
<213> ORGANISM: Artificial Sequence
<220> FEATURE:
<223> OTHER INFORMATION: Synthetic; SNP id: rs3746887, chr21: 41032844

<400> SEQUENCE: 26
cgctcttccg atctgactaa tgtccccgtg tcgctgg                         37

<210> SEQ ID NO 27
<211> LENGTH: 37
<212> TYPE: DNA
<213> ORGANISM: Artificial Sequence
<220> FEATURE:
<223> OTHER INFORMATION: Synthetic; SNP id: rs220312, chr21: 43518893

<400> SEQUENCE: 27
cgctcttccg atctctgaat agccagtgct gttctgg                         37

<210> SEQ ID NO 28
<211> LENGTH: 37
<212> TYPE: DNA
<213> ORGANISM: Artificial Sequence
<220> FEATURE:
<223> OTHER INFORMATION: Synthetic; SNP id: rs220312, chr21: 43519063

<400> SEQUENCE: 28
cgctcttccg atctgacacc acgtagtcac tgactgg                         37

<210> SEQ ID NO 29
<211> LENGTH: 37
<212> TYPE: DNA
<213> ORGANISM: Artificial Sequence
<220> FEATURE:
<223> OTHER INFORMATION: Synthetic; SNP id: rs4148973, chr21: 44323536

<400> SEQUENCE: 29
cgctcttccg atctctgttc agaagctcgt caggtgg                         37

<210> SEQ ID NO 30
<211> LENGTH: 37
<212> TYPE: DNA
<213> ORGANISM: Artificial Sequence -continued
<220> FEATURE:
<223> OTHER INFORMATION: Synthetic; SNP id: rs4148973, chr21: 44323703

<400> SEQUENCE: 30
cgctcttccg atctgacaag gaatgagagg cctctgg                37

<210> SEQ ID NO 31
<211> LENGTH: 37
<212> TYPE: DNA
<213> ORGANISM: Artificial Sequence
<220> FEATURE:
<223> OTHER INFORMATION: Synthetic; SNP id: rs2379206, chrX: 6995304

<400> SEQUENCE: 31
cgctcttccg atctctgagg aagatgtccg ggtctgg                37

<210> SEQ ID NO 32
<211> LENGTH: 37
<212> TYPE: DNA
<213> ORGANISM: Artificial Sequence
<220> FEATURE:
<223> OTHER INFORMATION: Synthetic; SNP id: rs2379206, chrX: 6995473

<400> SEQUENCE: 32
cgctcttccg atctgacatc cacctgcgga aacatgg                37

<210> SEQ ID NO 33
<211> LENGTH: 37
<212> TYPE: DNA
<213> ORGANISM: Artificial Sequence
<220> FEATURE:
<223> OTHER INFORMATION: Synthetic; SNP id: rs5934730, chrX: 9935444

<400> SEQUENCE: 33
cgctcttccg atctctgccc ttaccaccat aggatgg                37

<210> SEQ ID NO 34
<211> LENGTH: 37
<212> TYPE: DNA
<213> ORGANISM: Artificial Sequence
<220> FEATURE:
<223> OTHER INFORMATION: Synthetic; SNP id: rs5934730, chrX: 9935607

<400> SEQUENCE: 34
cgctcttccg atctgacttt ggttgtggtg ctgttgg                37

<210> SEQ ID NO 35
<211> LENGTH: 37
<212> TYPE: DNA
<213> ORGANISM: Artificial Sequence
<220> FEATURE:
<223> OTHER INFORMATION: Synthetic; SNP id: rs2071311, chrX: 30260896

<400> SEQUENCE: 35
cgctcttccg atctctgccc gtgaagagga aatctgg                37

<210> SEQ ID NO 36
<211> LENGTH: 37
<212> TYPE: DNA
<213> ORGANISM: Artificial Sequence
<220> FEATURE:
<223> OTHER INFORMATION: Synthetic; SNP id: rs2071311, chrX: 30261067

<400> SEQUENCE: 36
cgctcttccg atctgaccac aggaattgat agcgtgg                37

```
<210> SEQ ID NO 37
<211> LENGTH: 37
<212> TYPE: DNA
<213> ORGANISM: Artificial Sequence
<220> FEATURE:
<223> OTHER INFORMATION: Synthetic; SNP id: rs1801187, chrX: 32380928

<400> SEQUENCE: 37
cgctcttccg atctctgaaa tggctgcaaa tcgatgg                         37

<210> SEQ ID NO 38
<211> LENGTH: 37
<212> TYPE: DNA
<213> ORGANISM: Artificial Sequence
<220> FEATURE:
<223> OTHER INFORMATION: Synthetic; SNP id: rs1801187, chrX: 32381102

<400> SEQUENCE: 38
cgctcttccg atctgacgtc ctatctcttg ctcatgg                         37

<210> SEQ ID NO 39
<211> LENGTH: 37
<212> TYPE: DNA
<213> ORGANISM: Artificial Sequence
<220> FEATURE:
<223> OTHER INFORMATION: Synthetic; SNP id: rs2293948, chrX: 48418093

<400> SEQUENCE: 39
cgctcttccg atctctgagc agctcaagag cgagtgg                         37

<210> SEQ ID NO 40
<211> LENGTH: 37
<212> TYPE: DNA
<213> ORGANISM: Artificial Sequence
<220> FEATURE:
<223> OTHER INFORMATION: Synthetic; SNP id: rs2293948, chrX: 48418271

<400> SEQUENCE: 40
cgctcttccg atctgacgtg ggtaacggca taggtgg                         37

<210> SEQ ID NO 41
<211> LENGTH: 37
<212> TYPE: DNA
<213> ORGANISM: Artificial Sequence
<220> FEATURE:
<223> OTHER INFORMATION: Synthetic; chrY:3609387

<400> SEQUENCE: 41
cgctcttccg atctctgata ccagttactg gcaatgg                         37

<210> SEQ ID NO 42
<211> LENGTH: 37
<212> TYPE: DNA
<213> ORGANISM: Artificial Sequence
<220> FEATURE:
<223> OTHER INFORMATION: Synthetic; chrY: 3609547

<400> SEQUENCE: 42
cgctcttccg atctgacaca cagacagcga aagatgg                         37

<210> SEQ ID NO 43
<211> LENGTH: 37
<212> TYPE: DNA
<213> ORGANISM: Artificial Sequence
<220> FEATURE:
<223> OTHER INFORMATION: Synthetic; chrY: 7697094
```

<400> SEQUENCE: 43
cgctcttccg atctctgggc aggtgtcagg cttatgg				37

<210> SEQ ID NO 44
<211> LENGTH: 37
<212> TYPE: DNA
<213> ORGANISM: Artificial Sequence
<220> FEATURE:
<223> OTHER INFORMATION: Synthetic; chrY: 7697262

<400> SEQUENCE: 44
cgctcttccg atctgactgg tggcctggta aaagtgg				37

<210> SEQ ID NO 45
<211> LENGTH: 37
<212> TYPE: DNA
<213> ORGANISM: Artificial Sequence
<220> FEATURE:
<223> OTHER INFORMATION: Synthetic; chrY: 6792987

<400> SEQUENCE: 45
cgctcttccg atctctgtca gtcacacatc agtctgg				37

<210> SEQ ID NO 46
<211> LENGTH: 37
<212> TYPE: DNA
<213> ORGANISM: Artificial Sequence
<220> FEATURE:
<223> OTHER INFORMATION: Synthetic; chrY: 6793128

<400> SEQUENCE: 46
cgctcttccg atctgacata cagatcactg gaagtgg				37

<210> SEQ ID NO 47
<211> LENGTH: 37
<212> TYPE: DNA
<213> ORGANISM: Artificial Sequence
<220> FEATURE:
<223> OTHER INFORMATION: Synthetic; chrY: 14640461

<400> SEQUENCE: 47
cgctcttccg atctctgcga gttcttaatg agcttgg				37

<210> SEQ ID NO 48
<211> LENGTH: 37
<212> TYPE: DNA
<213> ORGANISM: Artificial Sequence
<220> FEATURE:
<223> OTHER INFORMATION: Synthetic; chrY: 14640619

<400> SEQUENCE: 48
cgctcttccg atctgacgct cattgtgttc catgtgg				37

<210> SEQ ID NO 49
<211> LENGTH: 37
<212> TYPE: DNA
<213> ORGANISM: Artificial Sequence
<220> FEATURE:
<223> OTHER INFORMATION: Synthetic; chrY: 22902850

<400> SEQUENCE: 49
cgctcttccg atctctggac attgaaggta gcgttgg				37

<210> SEQ ID NO 50

```
<211> LENGTH: 37
<212> TYPE: DNA
<213> ORGANISM: Artificial Sequence
<220> FEATURE:
<223> OTHER INFORMATION: Synthetic

<400> SEQUENCE: 50
cgctcttccg atctgacgag aaatcggagt tcattgg                              37

<210> SEQ ID NO 51
<211> LENGTH: 69
<212> TYPE: DNA
<213> ORGANISM: Artificial Sequence
<220> FEATURE:
<223> OTHER INFORMATION: Synthetic

<400> SEQUENCE: 51
aatgatacgg cgaccaccga gatctacact atagccttct ttccctacac gacgctcttc     60
cgatctctg                                                            69

<210> SEQ ID NO 52
<211> LENGTH: 69
<212> TYPE: DNA
<213> ORGANISM: Artificial Sequence
<220> FEATURE:
<223> OTHER INFORMATION: Synthetic

<400> SEQUENCE: 52
caagcagaag acggcatacg agatcgagta atgtgactgg agttcagacg tgtgctcttc     60
cgatctgac                                                            69

<210> SEQ ID NO 53
<211> LENGTH: 69
<212> TYPE: DNA
<213> ORGANISM: Artificial Sequence
<220> FEATURE:
<223> OTHER INFORMATION: Synthetic

<400> SEQUENCE: 53
caagcagaag acggcatacg agattctccg gagtgactgg agttcagacg tgtgctcttc     60
cgatctgac                                                            69

<210> SEQ ID NO 54
<211> LENGTH: 69
<212> TYPE: DNA
<213> ORGANISM: Artificial Sequence
<220> FEATURE:
<223> OTHER INFORMATION: Synthetic

<400> SEQUENCE: 54
caagcagaag acggcatacg agataatgag cggtgactgg agttcagacg tgtgctcttc     60
cgatctgac                                                            69

<210> SEQ ID NO 55
<211> LENGTH: 69
<212> TYPE: DNA
<213> ORGANISM: Artificial Sequence
<220> FEATURE:
<223> OTHER INFORMATION: Synthetic

<400> SEQUENCE: 55
caagcagaag acggcatacg agatggaatc tcgtgactgg agttcagacg tgtgctcttc     60
cgatctgac                                                            69
```

```
<210> SEQ ID NO 56
<211> LENGTH: 69
<212> TYPE: DNA
<213> ORGANISM: Artificial Sequence
<220> FEATURE:
<223> OTHER INFORMATION: Synthetic

<400> SEQUENCE: 56
caagcagaag acggcatacg agatttctga atgtgactgg agttcagacg tgtgctcttc        60
cgatctgac                                                               69

<210> SEQ ID NO 57
<211> LENGTH: 69
<212> TYPE: DNA
<213> ORGANISM: Artificial Sequence
<220> FEATURE:
<223> OTHER INFORMATION: Synthetic

<400> SEQUENCE: 57
caagcagaag acggcatacg agatacgaat tcgtgactgg agttcagacg tgtgctcttc        60
cgatctgac                                                               69
```

METHOD FOR DETERMINING GENETIC CONDITION OF FETUS

CROSS-REFERENCE TO RELATED APPLICATIONS

This application is a Continuation of PCT International Application No. PCT/JP2016/060444 filed on Mar. 30, 2016, which claims priority under 35 U.S.C. § 119(a) to Japanese Patent Application No. 2015-074318 filed on Mar. 31, 2015. The above application is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2017-11-16 1110-0574PUS1 ST25.txt" created on Nov. 16, 2017 and is 12,908 bytes in size. The sequence listing contained in this .txt file is part of the specification and is hereby incorporated by reference herein in its entirety.

BACKGROUND OF THE INVENTION

1. Field of the Invention

The present invention relates to a method for determining a genetic condition of a fetus.

2. Description of the Related Art

In the related art, an amniotic fluid test that investigates chromosomes of fetal cells in the amniotic fluid through amniocentesis has been performed as a prenatal diagnosis. However, for this method, a significant problem of having a possibility of miscarriage has been mentioned.

A prenatal diagnosis has recently been performed as a safe prenatal diagnosis through a method for analyzing fetus-derived cell-free deoxyribonucleic acid (DNA) which exists in maternal blood while being mixed with maternal cell-free DNA. This method has been attracting attention as a method which is noninvasive and can acquire fetal genetic information with high probability. A method for determining a polyploidy status of a chromosome in a fetus during pregnancy using genotype data measured from a mixed sample of mother-derived DNA of a fetus and fetus-derived DNA, and genotype data pieces from a mother or a father as necessary is disclosed in WO2003/074723A.

On the other hand, it has been known that fetal cells migrate into maternal blood and circulate the maternal body with the blood. In a case where it is possible to reliably analyze genomic DNA in such fetal cells with good reproducibility, it is possible to realize a prenatal diagnosis in which there is no possibility of miscarriage and which is safe and directly analyzes fetus-derived DNA.

However, it is understood that there is only about one fetal cell (for example, fetal nucleated red blood cell) existing in maternal blood, per several mL of maternal blood, and therefore, various methods for reliably obtaining fetal cells have been studied. In some cases, the number of fetal cells that can be obtained in a case where rare fetal cells are reliably sorted out using such well-known techniques is large or is limited to one.

Regarding an amplification technique for amplifying DNA in cells, a method for amplifying a plurality of target positions of interest through a multiplex polymerase chain reaction (PCR) using a plurality of primer sets, and detecting genetic diseases such as mutation and chromosomal abnormality is disclosed in WO2003/074723A. In addition, a method for amplifying a specific sequence of fetus-derived genomic DNA through a highly multi-targeted polymerase chain reaction and determining an allele frequency at each target genetic position using a sequencer is disclosed in WO2012/108920A.

The multiplex PCR is known as a reaction for simultaneously amplifying two or more amplification target regions in one reaction system. The multiplex PCR is known as a technique useful for efficiently amplifying amplification target regions from a small amount of DNA extracted from a trace amount of blood and typing a large number of single nucleotide polymorphisms (SNPs). A method for designing a primer for multiplex PCR which can efficiently amplify a plurality of amplification sites (targets) is disclosed in WO2008/004691A.

SUMMARY OF THE INVENTION

In order to determine a genetic condition of a fetus by isolating fetus-derived nucleated red blood cells and analyzing DNA in the obtained cells using a well-known technique, it is necessary to extract DNA from a single cell and amplify DNA to an amount required for analysis. Therefore, in many cases, whole genome amplification is performed.

However, although the whole genome amplification has an advantage of remarkably increasing the trace amount of genomic DNA which has been extracted from one cell, it is difficult to constantly maintain the amplification factor using an amplification region. Therefore, there is a disadvantage that a PCR product becomes biased through amplification.

For this reason, even if the whole genome amplification is not performed, a method for determining a genetic condition of a fetus is required which uniformly performs PCR amplification of an objective region accurately using the genomic DNA extracted from a single cell as a template.

An object of the present invention is to provide a method for determining a genetic condition of a fetus which uniformly performs amplification of an objective region accurately through a polymerase chain reaction (PCR).

The present inventors have conducted extensive studies to solve the above-described problems. As a result, they have found that a primer set can be obtained which is used for a polymerase chain reaction and can selectively amplify an objective gene region efficiently in a case where primers selected in both a first stage and a second stage are employed by performing: first stage selection based on a local alignment score obtained by evaluating formability of a primer dimer and obtaining a local alignment score through performing pairwise local alignment on a base sequence of a primer candidate under the condition that a partial sequence to be subjected to comparison includes the 3' terminal of a base sequence of a primer; and a second stage selection based on a global alignment score obtained by performing pairwise global alignment on a base sequence which has a predetermined sequence length and includes the 3' terminal of the base sequence of the primer candidate, and have completed the present invention.

That is, the present invention is the following (1) to (6).
(1) A method for determining a genetic condition of a fetus, the method comprising: an objective region selection step of selecting an objective region for determining the genetic condition, from regions on a human genome; a single cell isolation step of isolating a single cell from a maternal blood sample; a genomic DNA extraction step of extracting genomic DNA from the single cell; an amplification step performed through a polymerase chain reaction in which the objective region is amplified through the polymerase chain reaction using a primer set designed so as to amplify the objective region through the polymerase chain reaction using the genomic DNA extracted from the single cell as a template; and a DNA sequencing step of decoding a DNA base sequence of an amplification product of the objective region obtained through the polymerase chain reaction, in which the objective region selection step is performed before or after both steps of the single cell isolation step and the genomic DNA extraction step, or performed in parallel with both steps of the single cell isolation step and the genomic DNA extraction step, the primer set designed so as to amplify the objective region through the polymerase chain reaction is designed through a method for designing a primer set used for the polymerase chain reaction, the method for designing a primer set including a target region selection step of selecting a target region in which the primer set used for the polymerase chain reaction is designed, from the objective region, a primer candidate base sequence generation step of generating at least one base sequence of a primer candidate for amplifying the target region based on each base sequence in vicinity regions at both ends of the target region on the genome, a local alignment step of obtaining a local alignment score by performing pairwise local alignment on the base sequence of the primer candidate under a condition that a partial sequence to be subjected to comparison includes the 3' terminal of the base sequence of the primer candidate, a first stage selection step of performing first stage selection of the base sequence of the primer candidate based on the local alignment score obtained in the local alignment step, a global alignment step of obtaining a global alignment score by performing pairwise global alignment on a base sequence which has a predetermined sequence length and includes the 3' terminal of the base sequence of the primer candidate, a second stage selection step of performing second stage selection of a base sequence of the primer candidate based on the global alignment score obtained in the global alignment step, and a primer employment step of employing the base sequence of the primer candidate which has been selected in both of the first stage selection step and the second stage selection step as a base sequence of a primer for amplifying the target region, and in which both steps of the local alignment step and the first stage selection step are performed before or after both steps of the global alignment step and the second stage selection step, or performed in parallel with both steps of the global alignment step and the second stage selection step.

(2) The method for determining a genetic condition of a fetus according to (1), in which the primer set designed so as to amplify the objective region through the polymerase chain reaction is designed through a method for designing a primer set used for the polymerase chain reaction, the method for designing a primer set including a first target region selection step of selecting a first target region in which the primer set used for the polymerase chain reaction is designed, from the objective region, a first primer candidate base sequence generation step of generating at least one base sequence of a primer candidate for amplifying the first target region based on each base sequence in vicinity regions at both ends of the first target region on the genome, a first local alignment step of obtaining a local alignment score by performing pairwise local alignment on the base sequence of the primer candidate under a condition that a partial sequence to be subjected to comparison includes the 3' terminal of the base sequence of the primer candidate, a first step of first stage selection of performing first stage selection of the base sequence of the primer candidate based on the local alignment score obtained in the first local alignment step, a first global alignment step of obtaining a global alignment score by performing pairwise global alignment on a base sequence which has a predetermined sequence length and includes the 3' terminal of the base sequence of the primer candidate, a first step of second stage selection of performing second stage selection of the base sequence of the primer candidate based on the global alignment score obtained in the first global alignment step, a first primer employment step of employing the base sequence of the primer candidate which has been selected in both of the first step of first stage selection and the first step of second stage selection as a base sequence of a primer for amplifying the first target region, a second target region selection step of selecting a second target region in which the primer set used for the polymerase chain reaction is designed, from the objective region, a second primer candidate base sequence generation step of generating at least one base sequence of each primer candidate for amplifying the second target region based on each base sequence in vicinity regions at both ends of the second target region on the genome, a second local alignment step of obtaining a local alignment score by performing pairwise local alignment on the base sequence of the primer candidate for amplifying the second target region and the base sequence of the primer which has already been employed, under a condition that partial sequences to be subjected to comparison include the 3' terminal of the base sequence of the primer candidate and the 3' terminal of the base sequence of the primer which has already been employed, a second step of first stage selection of performing first stage selection of the base sequence of the primer candidate for amplifying the second target region based on the local alignment score obtained in the second local alignment step, a second global alignment step of obtaining a global alignment score by performing pairwise global alignment on base sequences which have a predetermined sequence length and include the 3' terminal of the base sequence of the primer candidate for amplifying the second target region and the 3' terminal of the base sequence of the primer which has already been employed, a second step of second stage selection of performing second stage selection of the base sequence of the primer candidate for amplifying the second target region based on the global alignment score obtained in the second global alignment step, and a second primer employment step of employing the base sequence of the primer candidate which has been selected in both of the second step of first stage selection and the second step of second stage selection as a base sequence of a primer for amplifying the second target region, in which both steps of the first local alignment step and the first step of first stage selection are performed before or after both steps of the first global alignment step and the first step of second stage selection, or performed in parallel with both steps of the first global alignment step and the first step of second stage selection, both steps of the second local alignment step and the second step of first stage selection are performed before or after both steps of the second global alignment step and the second step of second stage selection, or performed in parallel with both steps of the second global alignment step and the second step of second stage selection, and in a case where there are three or more of the target regions, the steps from the second target region selection step to the second primer employment step are repeated with respect to all of the target regions until a base sequence of a primer for amplifying each target region is employed.

(3) The method for determining a genetic condition of a fetus according to (1) or (2), in which the steps at least from the genomic DNA extraction step to the DNA sequencing step are repeated until a fetus-derived single cell can be isolated in the single cell isolation step.

(4) The method for determining a genetic condition of a fetus according to any one of (1) to (3), in which the genetic condition is a numerical abnormality of a chromosome.

(5) The method for determining a genetic condition of a fetus according to any one of (1) to (4), the method further comprising: a magnetic bead purification step of purifying the amplification product of the objective region obtained through the polymerase chain reaction, using magnetic beads, between the amplification step performed through the polymerase chain reaction and the DNA sequencing step.

(6) The method for determining a genetic condition of a fetus according to any one of (1) to (5), in which the number of times of sequence reading is further measured in the DNA sequencing step.

According to the present invention, it is possible to provide a method for determining a genetic condition of a fetus which uniformly performs amplification of an objective region accurately through a polymerase chain reaction.

In addition, according to the present invention, the determination of a gene sequence in the objective region is reliably performed efficiently in a short process.

BRIEF DESCRIPTION OF THE DRAWINGS

FIG. 2 shows a dot matrix obtained from the base sequences of SEQ ID No:1 and SEQ ID No:2.

DESCRIPTION OF THE PREFERRED EMBODIMENTS

Figure 1:
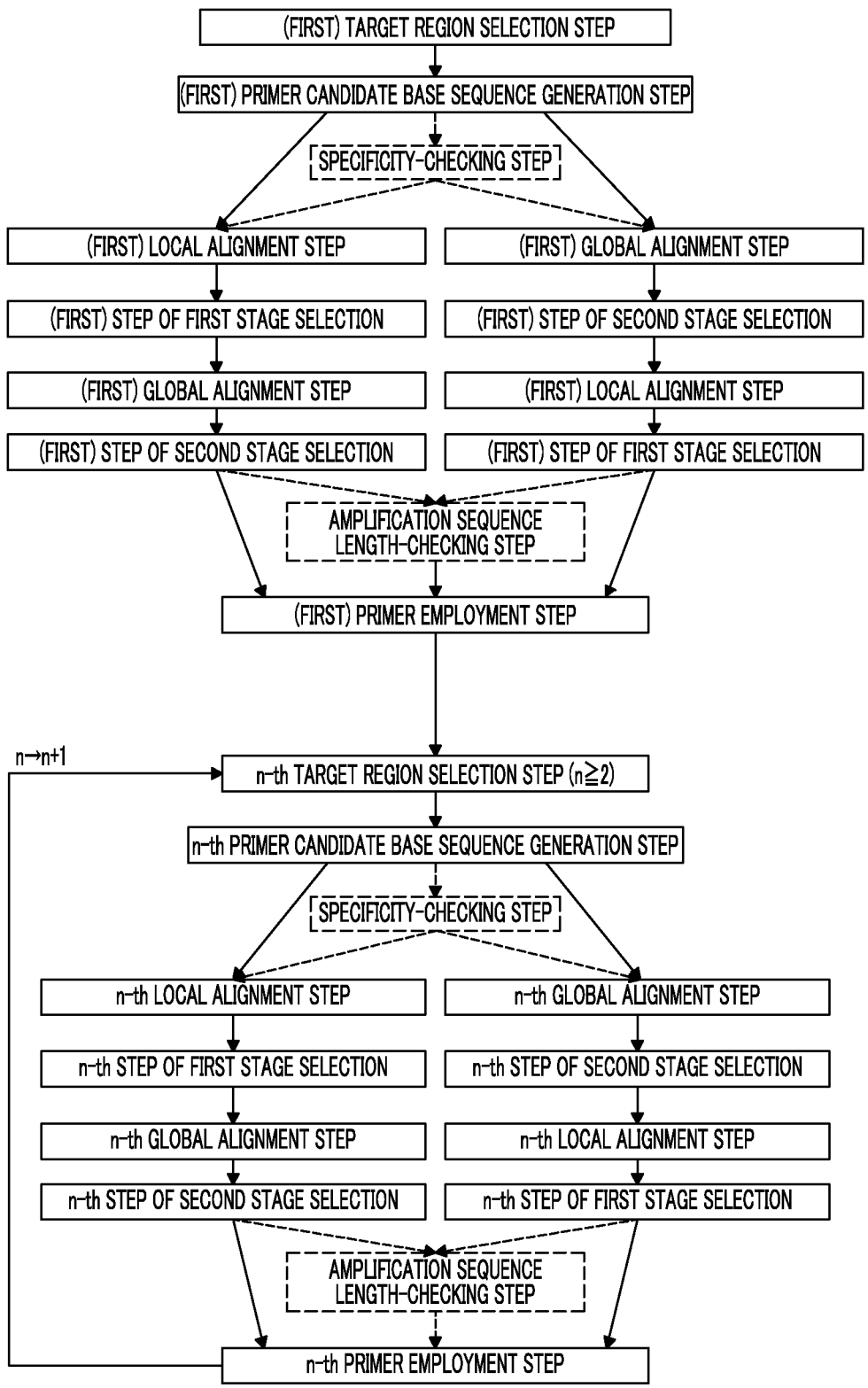
FIG. 1 is a block diagram representing a method for designing a primer and a primer set in the present invention.

The present invention generally relates to a technique of peeling cells which have been fixed on a substrate, extracting genomic DNA, and performing DNA amplification of a region to be amplified, to determine a genetic condition of fetus-derived nucleated red blood cells. More specifically, the present invention relates to a technique of shortening a work process by performing DNA amplification using primers designed such that complementarity between the primers is reduced in a case of performing the DNA amplification of the region to be amplified through a polymerase chain reaction, and solving the problem in that the amount of PCR amplification product among a plurality of cells varies.

A noninvasive prenatal diagnosis in the related art is a method for analyzing fetus-derived cell-free DNA which exists in maternal blood while being mixed with maternal cell-free DNA. This method is useful as a method for detecting a numerical abnormality of a fetal chromosome. However, the analysis is performed in a state where maternal cell-free DNA and fetus-derived cell-free DNA are mixed with each other. Therefore, this method has a disadvantage that it is difficult to determine a genetic condition other than the numerical abnormality. In contrast, the present invention is a technique of analyzing a fetus-derived single cell. In the present invention, a genetic polymorphism site and/or a somatic mutation site which are already well-known can be included in a detection region, and therefore, it is possible to determine a genetic condition which is not limited to the numerical abnormality.

In order to efficiently analyze an amplification product in sequence analysis of the amplification product, it is necessary to perform accurate amplification by reducing nonspecific products such as a primer dimer mixed in a sequence library. In the present invention, it is possible to reliably detect the presence or absence of a genetic abnormality of a fetus by improving the method for designing a primer and a primer set used for a polymerase chain reaction and uniformly amplifying various gene regions accurately also from an extremely small amount of DNA of a single cell.

Hereinafter, a method for determining a genetic condition of a fetus of the present invention will be described.

The method for determining a genetic condition of a fetus of the present invention is a method for determining a genetic condition of a fetus, the method including: an objective region selection step of selecting an objective region for determining the above-described genetic condition, from regions on a human genome; a single cell isolation step of isolating a single cell from a maternal blood sample; a genomic DNA extraction step of extracting genomic DNA from the above-described single cell; an amplification step performed through PCR in which the above-described objective region is amplified through the PCR using a primer set designed so as to amplify the above-described objective region through the PCR using genomic DNA extracted from the above-described single cell as a template; and a DNA sequencing step of decoding a DNA base sequence of an PCR amplification product of the above-described objective region, in which the objective region selection step is performed before or after both steps of the single cell isolation step and the genomic DNA extraction step, or performed in parallel with both steps of the single cell isolation step and the genomic DNA extraction step, and the primer set designed so as to perform PCR amplification on the objective region is designed through the method for designing a primer and a primer set which will be described in "<Method for Designing Primer and Primer Set>" to be described below.

<Objective Region Selection Step>

In the objective region selection step, an objective region for determining the genetic condition is selected from regions on a human genome.

(Regions on Human Genome)

The "regions on a human genome" in the present invention refers to a region on genomic DNA in which a site relating to genetic polymorphism, a single gene disease, a multifactorial disease, and/or cancer, and the like exist. Here, the length of a region is not particularly limited, and may be one or more bases.

The regions on a human genome from which an objective region is selected may exist in either a gene region or a non-gene region. Here, the gene region includes: a coding region in which a gene encoding proteins, a ribosomal ribonucleic acid (RNA) gene, a transfer RNA gene, and the like exist; and a non-coding region in which an intron dividing a gene, a transcription regulatory region, a 5' leader sequence, a 3' leader sequence, and the like exist. In addition, the non-gene region includes: a non-repetitive sequence such as a pseudogene, a spacer, a response element, and a replication origin; and a repetitive sequence such as a tandem repetitive sequence and an interspersed repetitive sequence.

Examples of genetic polymorphism include single nucleotide polymorphism (SNP), single nucleotide variant (SNV), short tandem repeat polymorphism (STRP), mutation, and insertion and/or deletion (indel).

The single gene disease is a disease caused by single gene abnormality. Examples of the abnormality include deletion or duplication of the gene, and/or substitution of a base in a gene, and insertion and/or deletion. A single gene that causes a single gene disease is called a "responsible gene".

The multifactorial disease is a disease in which a plurality of genes are involved in the onset. In some cases, a specific combination or the like of SNP may be related thereto. These genes are called "sensitive genes" in the sense that the genes are susceptible to a disease.

Cancer is a disease caused by gene mutation. Similarly to other diseases, there is hereditary (familial) cancer which is called a hereditary tumor (familial tumor) or the like.

The number of regions on a human genome is not particularly limited. This is because regions on a human genome are a candidate list in a case of selecting an objective region, and it is unnecessary to perform analysis for all the regions even if a large number of regions is listed.

(Objective Region)

The objective region is a region selected as a target for determining a genetic condition from the above-described regions on a human genome. Here, the purpose of selection is not limited to detection of genetic polymorphism, diseases, cancer, or the like related to each region, and may be detection of aneuploidy of a chromosome or the like. In addition, the number of purposes of the selection is not limited to one, and may be two or more.

The number of regions on a human genome to be selected as objective regions varies depending on a target genetic condition. The number of regions thereof is not particularly limited as long as it is greater than or equal to one region. However, the number of regions thereof is preferably greater than or equal to 3 regions, more preferably greater than or equal to 5 regions, and still more preferably greater than or equal to 10 regions.

(Determination of Genetic Condition)

Regarding a Mendelian hereditary disease in which an abnormality of a single gene becomes a cause of a disease, a causative gene to be detected is selected from an online mendelian inheritance in man (OMIM) database, and primers of several mutation sites to be examined are designed. A target gene region of genomic DNA which has been extracted from a fetal nucleated red blood cell is amplified using the designed primer set, and a base sequence of the amplification product is obtained using a sequencer. In comparison of the base sequence which has been decoded and a healthy reference genome, in a case where deletion, duplication, inversion, and/or translocation of a gene are recognized, it is expected that the fetus may have a genetic disease.

<Single Cell Isolation Step>

In the single cell isolation step, a single cell is isolated from a maternal blood sample.

The maternal blood sample is not particularly limited as long as the sample is a blood sample collected from a maternal body (pregnant woman), and maternal peripheral blood is preferable. Maternal body-derived nucleated red blood cells and fetus-derived nucleated red blood cells are included in the maternal peripheral blood in addition to white blood cells such as maternal body-derived eosinophils, neutrophils, basophils, mononuclear cells, and lymphocytes, and mature red blood cells having no nucleus. It has been known that fetus-derived nucleated red blood cells exist in maternal blood from about 6 weeks after pregnancy. For this reason, in the present invention, it is preferable to test peripheral blood of a pregnant woman after about 6 weeks of pregnancy.

The single cell is not particularly limited as long as the single cell is derived from a fetus, but a fetus-derived nucleated red blood cell is preferable. The fetus-derived nucleated red blood cell is a red blood cell precursor existing in maternal blood. During pregnancy of a mother, a red blood cell of a fetus may be nucleated. Since there is a chromosome in this red blood cell, a fetus-derived chromosome and a fetal gene become available using less invasive means. It has been known that this fetus-derived nucleated red blood cell exists at a rate of one per $10^6$ cells in the maternal blood, and the existence probability of the fetus-derived nucleated red blood cell in peripheral blood in a pregnant woman is extremely low.

(Concentration of Fetal Nucleated Red Blood Cell)

The density of blood cells in a maternal body including fetus-derived nucleated red blood cells is disclosed in WO2012/023298A. According to the disclosure, the assumed density of the fetus-derived nucleated red blood cells is about 1.065 to 1.095 g/mL. On the other hand, the density of blood cells of the maternal blood is about 1.070 to 1.120 g/mL in a case of red blood cells, about 1.090 to 1.110 g/mL in a case of eosinophils, about 1.075 to 1.100 g/mL in a case of neutrophils, about 1.070 to 1.080 g/mL in a case of basophils, about 1.060 to 1.080 g/mL in a case of lymphocytes, and about 1.060 to 1.070 g/mL in a case of mononuclear cells.

Fetus-derived nucleated red blood cells can be concentrated through density gradient centrifugation as a preferred embodiment in a case of isolating single cells. It is possible to use media such as Percoll (manufactured by GE Healthcare Bioscience) that is a silicic acid colloidal particle dispersion which is coated with polyvinylpyrrolidone and has a diameter of 15 to 30 nm, Ficoll-Paque (manufactured by GE Healthcare Bioscience) which is a neutral hydrophilic polymer which is rich in side chains and formed of sucrose, and/or Histopaque (manufactured by Sigma-Aldrich Co. LLC.) which is a solution using polysucrose and sodium diatrizoate, as a first medium and a second medium.

In the present invention, it is preferable to use Percoll and Histopaque. A product with a density of 1.130 g/cm$^3$ (specific gravity of 1.130) is commercially available as Percoll, and it is possible to prepare a medium with a target density (specific gravity) by diluting the product. In addition, a medium with a density of 1.077 g/cm$^3$ (specific gravity of 1.077) and a medium with a density of 1.119 g/cm$^3$ (specific gravity of 1.119) are commercially available as Histopaque, and it is possible to prepare a medium with a target density (specific gravity) by mixing these media with each other. By using Percoll and Histopaque, it is possible to prepare a first medium and a second medium.

The density of media to be stacked is set in order to separate fetus-derived nucleated red blood cells having a density of about 1.065 to 1.095 g/mL from other blood cell components in a maternal body. The central density of fetus-derived nucleated red blood cells is about 1.080 g/mL. Therefore, in a case where two media (first medium and second medium) having different densities interposing the central density are prepared and are made to be adjacent to and overlap each other, it is possible to collect fractions having the desired fetus-derived nucleated red blood cells on an interface between the media. It is preferable that the density of the first medium is set to be 1.080 g/mL to 1.100 g/mL and the density of the second medium is set to be 1.060 g/mL to 1.080 g/mL. It is more preferable that the density of the first medium is set to be 1.080 g/mL to 1.090 g/mL and the density of the second medium is set to be 1.065 g/mL to 1.080 g/mL. As a specific embodiment, it is preferable to separate plasma components, eosinophils, and mononuclear cells from the desired fractions to be collected, by setting the density of the first medium to 1.085 g/mL and the density of the second medium to 1.075 g/mL. In addition, by setting the densities of the media, it is also possible to partially separate red blood cells, neutrophils, and lymphocytes therefrom. In the present invention, the type of the first medium and the type of the second medium may be the same as or different from each other. However, the types of the media are preferably the same as each other.

(Isolation of Nucleated Red Blood Cell Candidate)

In order to obtain a nucleated red blood cell candidate from maternal blood, it is possible to prepare a substrate (blood cell specimen) coated with blood cells by coating the top of the substrate with blood and drying the blood. A transparent medium is preferably used as this substrate and slide glass is more preferably used as this substrate.

It is possible to sort out a fetus-derived nucleated red blood cell candidate based on the information on the shape of blood cells obtained from the blood cell specimen. As a preferred embodiment, it is possible to sort out a fetus-derived nucleated red blood cell candidate using a ratio of the area of a nuclear region to the area of cytoplasm of a cell, the degree of circularity of a nucleus, and/or the area of a nuclear region, and the like. Particularly, it is preferable to sort out a cell in which the ratio of the area of a nuclear region to the area of cytoplasm or the degree of circularity of a nucleus satisfies the conditions, as a fetus-derived nucleated red blood cell candidate.

As an example, in the present invention, it is preferable to sort out cells in which the ratio "N/C" of the area of a nuclear region to the area of cytoplasm satisfies Formula (1).

$$0.25 < N/C < 1.0 \quad (1)$$

However, in Formula (1), "N" represents the area of a nuclear region of a cell on which image analysis is to be performed and "C" represents the area of cytoplasm of a cell on which image analysis is to be performed.

As another example, in the present invention, it is preferable to sort out cells in which the ratio "N/L$^2$" of the area of the nuclear region to the square of the length of the major axis of a nucleus satisfies Formula (2).

$$0.65 < N/L^2 < 0.785 \quad (2)$$

However, in Formula (2), "N" represents the area of a nuclear region of a cell on which image analysis is to be performed and "L" represents the length of a major axis of a nucleus of a cell on which image analysis is to be performed, that is, the length of a major axis of an ellipse circumscribing a cell nucleus which has a complicated shape.

A system of sorting out a fetus-derived nucleated red blood cell candidate using information on the shape of cells is equipped with an optical microscope, a digital camera, a stage for slide glass, an optical transfer system, an image processing PC, a control PC, and a display. The optical transfer system includes an objective lens and a CCD camera. The image processing PC includes a processing system of performing data analysis and storing of data. The control PC includes a control system of controlling the position of a stage for slide glass or controlling the entire processing.

A protein existing in a red blood cell in the blood of all vertebrates including human beings is hemoglobin. The presence or absence of hemoglobin in a nucleated red blood cell is different from the presence or absence of hemoglobin in a white blood cell which is a type of nucleated cell in blood. Hemoglobin in a case of being bonded to oxygen is oxygenated hemoglobin exhibiting clear red color, and hemoglobin in a case of not being bonded to oxygen is reduced hemoglobin exhibiting dark red color. Hemoglobin having different oxygen bonding amounts flows in the arteries and the veins. Hemoglobin has absorption at 380 nm to 650 nm. Therefore, it is possible to detect hemoglobin using information of at least one monochromatic light beam caused by the difference in the absorbance of this wavelength range. It is preferable to use monochromatic light in order to check the presence or absence of hemoglobin. It is possible to select light with a single wavelength in a wavelength range of 400 nm to 500 nm or monochromatic light in a wavelength range of 525 nm to 580 nm, in which the absorbance of hemoglobin is large. The absorption coefficients of these wavelength ranges show high values due to the existence of hemoglobin. Therefore, the ratio of each absorption coefficient of these wavelength ranges to the absorption coefficient of cytoplasm of a white blood cell becomes greater than or equal to 1.

As an embodiment, it is possible to identify a cell in which a cell nucleus having a nearly circular shape exists and which has hemoglobin, as a nucleated red blood cell candidate. Furthermore, in fetus-derived nucleated red blood cells and adult-derived nucleated red blood cells, hemoglobin of a fetus is hemoglobin F (HbF) and hemoglobin of an adult is hemoglobin A (HbA). Therefore, it is possible to sort out fetus-derived nucleated red blood cells using the difference in spectral characteristics caused by different oxygen bonding abilities.

In a case of measuring the absorption coefficient of cytoplasm, it is possible to use a microspectrophotometer. The microspectrophotometer is a photometer in which the same principle as that of a usual spectrophotometer is used for an optical system of a microscope, and it is possible to use a commercially available device.

In the preferred embodiment of the present invention, it is possible to obtain a cell by peeling a single cell from the top of a transparent substrate using a micromanipulator.

In some cases, it is impossible to define whether the isolated nucleated red blood cell is derived from a fetus or from a maternal body (pregnant woman) depending on only the information on the shape and/or the absorbance of the cell. However, in the present invention, it is possible to discriminate the origin of the isolated nucleated red blood cell through polymorphism analysis using SNP and/or short tandem repeat (STR: short tandem repeat sequence) or the like, and through DNA analysis such as checking the presence of a Y chromosome. The DNA analysis can be performed simultaneously with the determination of a genetic condition as described in "(identification of fetal nucleated red blood cells)" in a DNA sequencing step to be described below.

<Genomic DNA Extraction Step>

In the genomic DNA extraction step, genomic DNA is extracted from a single cell isolated in the above-described "<Single Cell Isolation Step>".

<PCR Amplification Step>

In the PCR amplification step, an objective region is subjected to PCR amplification using a primer set which has been designed so as to perform PCR amplification of the objective region using the genomic DNA extracted in the above-described "<Genomic DNA Extraction Step>" as a template. The method for designing the "primer set which has been designed so as to perform PCR amplification of the objective region" will be described in detail in "<Method for Designing Primer and Primer set>" to be described below.

(Polymerase Chain Reaction)

In the polymerase chain reaction, template DNA is repeatedly replicated using DNA polymerase. The replication is started using polymerase by adding a short DNA primer hybridizing to the template DNA in a starting portion and an ending portion of a DNA base sequence to be amplified. Two chains of template double-stranded DNA are dissociated and are individually replicated every time the replication is repeated.

In multiplex PCR, it is possible to use heat-resistant DNA polymerase and a reaction buffer which are generally used in PCR. However, in some cases, each primer pair has a different temperature annealing to template DNA, and therefore, it is necessary to examine reaction conditions. For this reason, it is preferable to use heat-resistant DNA polymerase and reaction buffer which are optimized for multiplex PCR. In the present invention, it is more preferable to cause a reaction using MULTIPLEX PCR ASSAY KIT (manufactured by TAKARA BIO INC.).

The details of the method for designing a primer and a primer set will be described below. Therefore, the outline of a case of detecting aneuploidy of chromosome 13, chromosome 18, and/or chromosome 21 will be described herein as an example.

Regarding the number of objective regions, in the case of detecting aneuploidy of chromosome 13, chromosome 18, and/or chromosome 21, target regions in necessary regions are selected from DNA sequence regions specific to the above-described chromosomes in accordance with an examination, base sequences of primer candidates for amplifying each of the target regions are generated, and a primer candidate having low complementarity between primer base sequences is selected. Accordingly, the amplification properties of an objective region are significantly improved even with respect to a trace amount of genomic DNA of a single cell or the like.

Although next generation sequencer technology is rapidly evolving, a very complicated process is required for preparing a sample to be used for sequence analysis. In a case of the most widely applied genome analysis, pretreatment of a sample requires processes such as (1) DNA fragmentation, (2) DNA size selection, (3) smoothing processing of DNA terminals, (4) addition of an adaptor sequence to DNA terminals, (5) Purification of DNA, and (6) amplification of DNA, after extracting nucleic acids from the sample.

The complicated sample preparation step requires time and labor, and it is necessary to check whether the step has been appropriately performed. In addition, bias is caused in each step. Therefore, it is necessary to reduce this bias in a case of using a sample as a diagnostic tool in a medical field in which particularly high precision and accuracy of a result is required.

In order to solve these problems, in the present invention, it is possible to perform more uniform amplification of an objective region selected for discriminating a genetic condition by performing multiplex PCR using a primer designed through a specific method to be described below. Furthermore, it is possible to more effectively collect amplification products by purifying a PCR product using magnetic beads. Contaminants such as surplus primers, deoxynucleotides (dNTPs), and enzymes remain in a PCR reaction solution. Therefore, in some cases, the remaining contaminants become an obstacle in a case of obtaining highly accurate sequence data. However, it is possible to perform sufficient purification while significantly suppressing loss of a PCR amplification product by purifying the PCR amplification product using magnetic beads. In this case, it is preferable to use a method for reliably detecting the presence or absence of a genetic abnormality of a fetus by uniformly amplifying various gene regions accurately through only a simple sample preparation step such as (1) amplification of DNA and (2) purification of DNA even from an extremely small amount of DNA of a single cell.

Measurement of the amount of DNA amplified can be performed, for example, using NANODROP (manufactured by Thermo Fisher Scientific) which is an ultra-trace spectrophotometer for measuring the absorbance at a wavelength of 260 nm, Agilent 2100 BIOANALYZER (manufactured by Agilent Technologies) in which a laser fluorescence detection method is used, Quantus FLUOROMETER (manufactured by Promega Corporation) for quantitatively determining double-stranded DNA through a fluorescence method, or the like.

<PCR Amplification Product Purification Step>

Enzymes, nucleotides, salts, and other impurities coexist in a reaction liquid containing a PCR amplification product, and therefore are preferably removed.

A method in which phenol, chloroform, and ethanol are used, a method for selectively adsorbing nucleic acids on a silica carrier such as a silica membrane filter in the presence of chaotropic salts, a method in which a phenomenon that nucleic acids are selectively bonded to magnetic beads modified with carboxyl groups in the presence of polyethylene glycol (PEG) is used, and the like are known as examples of the method for purifying nucleic acids.

As the preferred embodiment of the present invention, it is possible to select a method for purifying a multiplex PCR amplification product in which magnetic beads are used.

(Magnetic Bead Purification Step)

It is possible to efficiently analyze only an objective region by purifying a PCR amplification product using magnetic beads which are paramagnetic microbeads. In the purification method in which magnetic beads are used, it is possible to efficiently remove contaminants such as enzymes, dNTPs, PCR primers, primer dimers, and salts by reversibly bonding nucleic acids to the surfaces of particles of the magnetic beads, adsorbing the magnetic beads with a magnet, and separating an amplified DNA fragment and liquid from each other. The method in which magnetic beads are used has less sample loss and higher efficiency of removing contaminants compared to other purification methods. As a result, it is possible to efficiently analyze only an objective region in the DNA sequencing step.

The magnetic beads are commercially available and it is possible to use, for example, AMPure XP KIT (manufactured by BECKMAN COULTER), NucleoMag (manufactured by TAKARA BIO INC.), or EpiNext DNA Purification HT System (manufactured by Epigentek Group Inc.). Among them, it is preferable to perform purification using AMPure XP KIT (manufactured by BECKMAN COULTER).

<DNA Sequencing Step>

It is desirable to use a next generation sequencer, particularly Miseq (manufactured by Illumina, Inc.) for analyzing a sequence of a PCR amplification product. In a case of sequencing a plurality of multiplex PCR products using the next generation sequencer "Miseq", it is necessary to add P5 and P7 sequences, which are used for hybridizing to a sample identification sequence (index sequence) formed of 6 to 8 bases, and an oligonucleotide sequence on the top of a Miseq flow cell, to each of the multiplex PCR products. By adding these sequences thereto, it is possible to measure up to 96 types of multiplex PCR products at a time.

It is possible to use an adapter ligation method or a PCR method as the method for adding an index sequence and P5 and P7 sequences to both terminals of the multiplex PCR products.

In addition, in a case of mixing a plurality of multiplex PCR products and measuring the plurality of multiplex PCR products using Miseq, it is desirable to quantitatively determine each PCR product accurately. It is also possible to use Agilent 2100 BIOANALYZER (manufactured by Agilent Technologies), or Quantus FLUOROMETER (manufactured by Promega KK.) as the method for quantitatively determining PCR products. However, a method for measuring the multiplex PCR products through a quantitative PCR method is more preferable. It is preferable to perform quantitative determination as the quantitative method in the present invention using KAPA Library Quantification KIT manufactured by NIPPON Genetics Co, Ltd.

As the method for analyzing sequence data obtained using Miseq, it is preferable to map the sequence data in a well-known human genome sequence using Burrows-Wheeler Aligner (BWA: Li, H., et al., "Fast and accurate short read alignment with Burrows-Wheeler transform", Bioinformatics, 2009, Vol. 25, No. 14, PP. 1754-1760; and Li, H., et al., "Fast and accurate long-read alignment with Burrows-Wheeler transform", Bioinformatics, 2010, Vol. 26, No. 5, PP. 589-595). As means for analyzing a genetic abnormality, it is preferable to analyze genetic mutation or quantitative determination of the number of chromosomes, using SAMtools (Li, Heng, et al., "The Sequence Alignment/Map format and SAMtools", Bioinformatics, 2009, Vol. 25, No. 16, PP. 2078-2079; SAM is derived from "Sequence Alignment/Map") and/or BEDtools (Quinlan, A. R., et al., "BEDtools: a flexible suite of utilities for comparing genomic features", Bioinformatics, 2010, Vol. 26, No. 6, PP. 841-842).

(Determination of Number of Times of Sequence Reading)

In the DNA sequencing step, it is desirable to measure the number of times of sequence reading.

For example, regarding DNA fragments in which fetal nucleated red blood cells are identified and which are obtained by performing PCR amplification of a target region, the amplification amount (number of times of sequence reading) of amplification product having a sequence of a region of 140 bp to 180 bp which has been previously determined can be obtained using a sequencer. Regarding a cell which has been identified as a mother-derived nucleated red blood cell, the amplification amount (number of times of sequence reading) of amplification product having a sequence of a region of 140 bp to 180 bp which has been previously determined is obtained as a standard (or a reference) using the sequencer. In a case where fetuses are in normal states, it is expected that the ratio of the amplification amount (number of times of sequence reading) of mother-derived amplification product to the amplification amount (number of times of sequence reading) of fetus-derived amplification product becomes almost 1:1. In a case where fetuses have a disease which is trisomy derived from an amplified chromosome, it is expected that the ratio thereof becomes almost 1:1.5 (or 2:3).

In the present invention, the proportions of the amount (number of times of sequence reading) of fetus-derived PCR amplification products to the amount (number of times of sequence reading) of mother-derived PCR amplification products which have been collected from a plurality of pregnant maternal bodies in a case where the mothers are pregnant with normal fetuses are obtained plural times, and the distribution thereof is obtained. In addition, the proportions of the amount (number of times of sequence reading) of fetus-derived amplification products to the amount (number of times of sequence reading) of mother-derived amplification products in a case where the mothers are pregnant with fetuses with trisomy are obtained, and the distribution thereof is obtained. It is also possible to set a cutoff value in a region where these two distributions do not overlap. After comparing the cutoff value which has previously been determined with a result in which the proportion of the amplification products is obtained, it is also possible to interpret inspection results that the fetuses are normal in a case where the proportion thereof is less than or equal to the cutoff value, and the fetuses have trisomy in a case where the proportion thereof is greater than or equal to the cutoff value.

In a case where no results are obtained, the method of the present invention may be performed again while returning to the single cell isolation step of isolating a single cell from a maternal blood sample.

(Confirmation on whether or not Isolated Nucleated Red Blood Cell is Derived from Fetus)

Whether or not isolated nucleated red blood cells are derived from a fetus may be confirmed to determine that determination of a genetic condition of a fetus-derived single cell is performed.

It is known that mother-derived nucleated red blood cells and fetus-derived nucleated red blood cells coexist in nucleated red blood cells of peripheral blood collected from a pregnant maternal body. The method of the present invention can identify fetus-derived nucleated red blood cells while determining a genetic condition of a fetus. In general, a method for detecting genetic polymorphism existing in an allele is performed as a method for identifying individual differences in a gene sequence. For example, it is also possible to use STR as a type of genetic polymorphism for father-child discrimination. In addition, it is also possible to use SNPs of which a single base in a genome base sequence is mutated and which is observed at a frequency of 1% or more. In the present invention, it is also possible to identify fetal cells and maternal cells using a next generation sequencer depending on the presence or absence of cells having STR or SNPs different from each other in nucleated red blood cells. In addition, the determination on whether nucleated red blood cells are derived from a fetus separately using supplementary information for determining a genetic condition can be performed, for example, by obtaining mother-derived white blood cells and analyzing STR or SNPs in the same manner.

In addition, in a case where it is confirmed that a fetus is a male fetus through an ultrasound inspection before collecting nucleated red blood cells, it is possible to determine whether or not the nucleated red blood cells are derived from a fetus by detecting the presence or absence of the Y chromosome in the collected nucleated red blood cells. In general, a Fluorescent in situ hybridization (FISH) method using a Y chromosome-specific fluorescent probe is known as the method for detecting the presence or absence of the Y chromosome in the collected cells. For example, CEP X/Y DNA PROBE KIT (manufactured by Abbott) is used. In the present invention, it is preferable to identify that the nucleated red blood cells are derived from a male fetus by preparing a primer having a Y chromosome-specific base sequence and checking the presence or absence of amplification of the primer through PCR.

<Method for Designing Primer and Primer Set>

In general, the method for designing a primer and a primer set which is one of the characteristics of the present invention obtains primer groups which include target regions as targets to be amplified and do not become complementary to each other, by selecting a plurality of specific target regions, searching vicinity base sequences, checking complementarity with each extracted primer set, and selecting base sequences having low complementarity. The checking of the complementarity of primer sequences has a characteristic in that primer groups are generated such that complementarity of a whole sequence becomes low using local alignment and the complementarity with respect to ends of primer sequences becomes low using global alignment. The details will be described below.

A first embodiment of a method for designing a primer and a primer set according to the present invention includes the following steps: (a) a target region selection step of selecting a target region in which the primer set used for the polymerase chain reaction is designed, from an objective region for determining a genetic condition which is selected in the objective region selection step; (b) a primer candidate base sequence generation step of generating at least one base sequence of a primer candidate for amplifying the above-described target region based on each base sequence in vicinity regions at both ends of the above-described target region on a genome; (c) a local alignment step of obtaining a local alignment score by performing pairwise local alignment on the base sequence of the above-described primer candidate under a condition that a partial sequence to be subjected to comparison includes the 3' terminal of the base sequence of the above-described primer candidate; (d) a first stage selection step of performing first stage selection of the base sequence of the above-described primer candidate based on the local alignment score obtained in (c) local alignment step; (e) a global alignment step of obtaining a global alignment score by performing pairwise global alignment on a base sequence which has a predetermined sequence length and includes the 3' terminal of the base sequence of the above-described primer candidate; (f) a second stage selection step of performing second stage selection of a base sequence of the above-described primer candidate based on the global alignment score obtained in (e) global alignment step; and (g) a primer employment step of employing the base sequence of the primer candidate which has been selected in both (d) first stage selection step and (f) second stage selection step as a base sequence of a primer for amplifying the above-described target region, in which both steps of (c) local alignment step and (d) first stage selection step are performed before or after both steps of (e) global alignment step and (f) second stage selection step, or performed in parallel with both steps of (e) global alignment step and (f) second stage selection step.

Each of the steps of the first embodiment of the method for designing a primer and a primer set according to the present invention will be described in detail.

(a) Target Region Selection Step

The target region selection step is shown in a block diagram of FIG. 1 as "(FIRST) TARGET REGION SELECTION STEP".

The target region selection step is a step of selecting a target region in which a primer set used for a polymerase chain reaction is designed, from an objective region for determining a genetic condition of a fetus which has been selected from regions on a human genome in the objective region selection step.

(Target Region)

The target region is a region selected as a target for designing a primer set used for a polymerase chain reaction, from the above-described objective region.

(Polymerase Chain Reaction)

In the present invention, the polymerase chain reaction (PCR) is a reaction for synthesizing DNA from template DNA using DNA polymerase. Unlike intracellular DNA synthesis, one or more oligonucleotides, in general, two or more oligonucleotides which are called primers are required for synthesizing DNA in PCR. In some cases, a combination of primers simultaneously used in a PCR reaction system is referred to as a primer set.

PCR can be easily extended from a simple system in which a region is amplified using a primer set which is a pair to a complex system (multiplex PCR) in which a plurality of regions are simultaneously amplified using a plurality of pairs of primer sets.

The advantage of PCR is that it is possible to selectively amplify only a desired region from extremely long DNA molecules of a human genome (3 billion base pairs). In addition, it is possible to obtain a sufficient amount of an amplification product of a desired region using an extremely trace amount of genomic DNA as a template.

In addition, another example of an advantage of PCR includes a short period of time of about 2 hours generally required for the amplification even though the period of time depends on the programs.

Still another example of the advantage of PCR is that the process is simple, and therefore, it is possible to perform the amplification using a fully automated desktop device.

(b) Primer Candidate Base Sequence Generation Step

The primer candidate base sequence generation step is shown in the block diagram of FIG. 1 as "(FIRST) PRIMER CANDIDATE BASE SEQUENCE GENERATION STEP".

The primer candidate base sequence generation step is a step of generating at least one base sequence of a primer candidate for amplifying a target region based on each base sequence in vicinity regions at both ends of the target region on a genome.

The vicinity regions of the target region are collectively called regions on the outside of the 5' terminal of the target region and regions on the outside of the 3' terminal of the target region. The inside of the target region is not included in the vicinity regions.

The length of a vicinity region is not particularly limited, but is preferably less than or equal to a length that can be expanded through PCR and more preferably less than or equal to the upper limit of a fragment length of DNA for which amplification is desired. A length facilitating application of concentration selection and/or sequence reading is particularly preferable. The length of a vicinity region may be appropriately changed in accordance with the type of enzyme (DNA polymerase) used for PCR. The specific length of a vicinity region is preferably about 20 to 500 bases, more preferably about 20 to 300 bases, still more preferably about 20 to 200 bases, and particularly preferably about 50 to 200 bases.

In addition, in a case of generating a base sequence of a primer candidate, points, such as the length of a primer, the GC content (referring to a total mole percentage of guanine (G) and cytosine (C) in all nucleic acid bases), a Tm value (which is a temperature at which 50% of double-stranded DNA is dissociated and becomes single-stranded DNA, and in which Tm is derived from a melting temperature), and deviation of a sequence, to be taken into consideration in a general method for designing a primer are the same.

The length of a primer (the number of nucleotides) is not particularly limited, but is preferably 15 mer to 45 mer, more preferably 20 mer to 45 mer, and still more preferably 20 mer to 30 mer. In a case where the length of a primer is within this range, it is easy to design a primer excellent in specificity and amplification efficiency.

The GC content is not particularly limited, but is preferably 40 mol % to 60 mol % and more preferably 45 mol % to 55 mol %. In a case where the GC content is within this range, a problem such as a decrease in the specificity and the amplification efficiency due to a high-order structure is less likely to occur.

The Tm value is not particularly limited, but is preferably within a range of 50° C. to 65° C. and more preferably within a range of 55° C. to 65° C.

The Tm value can be calculated using software such as OLIGO Primer Analysis Software (manufactured by Molecular Biology Insights) or Primer3 (http://www-genome.wi.mitedu/ftp/distribution/software/).

In addition, the Tm value can also be obtained through calculation using the following formula from the number of A's, T's, G's, and C's (which are respectively set as nA, nT, nG, and nC) in a base sequence of a primer.

$$Tm \text{ value } (° C.) = 2(nA+nT) + 4(nC+nG)$$

The method for calculating the Tm value is not limited thereto and can be calculated through various well-known methods in the related art.

The base sequence of a primer candidate is preferably set as a sequence in which there is no deviation of bases as a whole. For example, it is desirable to avoid a GC-rich sequence and a partial AT-rich sequence.

In addition, it is also desirable to avoid continuation of T and/or C (polypyrimidine) and continuation of A and/or G (polypurine).

Furthermore, it is preferable that a 3' terminal base sequence avoids a GC-rich sequence or an AT-rich sequence. G or C is preferable for a 3' terminal base, but is not limited thereto.

(Specificity-Checking Step)

If desired, a specificity-checking step of evaluating specificity of a base sequence of a primer candidate may be performed based on sequence complementarity with respect to genomic DNA of a base sequence of each primer candidate which has been generated in the above-described (b) Primer Candidate Base Sequence Generation Step.

In the specificity check, in a case where local alignment of a base sequence of genomic DNA and a base sequence of a primer candidate is performed and a local alignment score is less than a predetermined value, it is possible to evaluate that the complementarity of the base sequence of the primer candidate with respect to genomic DNA is low and the specificity of the base sequence of the primer candidate with respect to genomic DNA is high. Here, it is desirable to perform local alignment on also a complementary chain of genomic DNA. This is because genomic DNA is double-stranded whereas the primer is single-stranded DNA. In addition, a base sequence complementary to the base sequence of the primer candidate may be used instead of the base sequence of the primer candidate. The complementarity can be considered as homology with respect to a complementary chain.

In addition, homology search may be performed on genomic DNA base sequence database using the base sequence of the primer candidate as a query sequence. Examples of a homology search tool include Basic Local Alignment Search Tool (BLAST) (Altschul, S. A., et al., "Basic Local Alignment Search Tool", Journal of Molecular Biology, 1990, October, Vol. 215, pp. 403-410) and FASTA (Pearson, W. R., et al., "Improved tools for biological sequence comparison", Proceedings of the National Academy of Sciences of the United States of America, National Academy of Sciences, 1988, April, Vol. 85, pp. 2444-2448). It is possible to obtain local alignment as a result of performing the homology search.

All of the scoring system and a threshold value of a local alignment score are not particularly limited, and can be appropriately set in accordance with the length of a base sequence of a primer candidate and/or PCR conditions, and the like. In a case of using a homology search tool, a default value of the homology search tool may be used.

For example, as the scoring system, it is considered that complementary base (match)=+1, non-complementary base (mismatch)=−1, and insertion and/or deletion (gap penalty)=−3 are employed and the threshold value is set to be +15.

In a case where a base sequence of a primer candidate has complementarity to a base sequence at an unexpected position on genomic DNA but has low specificity thereto, in some cases, an artifact is amplified instead of a target region in a case where PCR is performed using a primer of the base sequence of a primer candidate. Therefore, the case where the base sequence of the primer candidate has complementarity to the base sequence at an unexpected position on genomic DNA but has low specificity thereto is excluded.

(c) Local Alignment Step

The local alignment step is shown in the block diagram of FIG. 1 as "(FIRST) LOCAL ALIGNMENT STEP".

The local alignment step is a step of obtaining a local alignment score by performing pairwise local alignment on all pairs each consisting of two base sequences extracted from the base sequences of the primer candidates which have been generated in the above-described (b) Primer Candidate Base Sequence Generation Step and is used for amplifying a target region, under a condition that partial sequences to be subjected to comparison include the 3' terminals of the base sequences of the primer candidates.

A combination of pairs of base sequences to be subjected to local alignment may be a combination selected while allowing overlapping, or may be a combination selected without allowing overlapping. However, in a case where formability of a primer dimer between primers of an identical base sequence has not yet been evaluated, the combination selected while allowing overlapping is preferable.

The total number of combinations is "$_mH_2 = {}_{m+1}C_2 = (m+1)!/2(m-1)!$" in a case where the selection is performed while allowing overlapping, and is "$_mC_2 = m(m-1)/2$" in a case where the selection is performed without allowing overlapping, in which the number of base sequences which have been generated in the above-described (b) Primer Candidate Base Sequence Generation Step is set to be m.

In a case where both steps of (e) Global Alignment Step and (f) Second Stage Selection Step to be described below are performed first, the present step and (d) First Stage Selection Step to be described below may be performed on primer candidates selected in (f) Second Stage Selection Step.

Local alignment is alignment which is performed on a partial sequence and in which it is possible to locally check a portion with high complementarity.

However, in the present invention, the local alignment is different from local alignment usually performed on a base sequence, and is designed such that partial sequences to be subjected to comparison include the 3' terminals of both base sequences by performing local alignment under the condition that the "partial sequences to be subjected to comparison include the 3' terminals of the base sequences". Furthermore, in the present invention, an embodiment is preferable in which partial sequences to be subjected to comparison include the 3' terminals of both base sequences by performing local alignment under the condition that the "partial sequences to be subjected to comparison include the 3' terminals of the base sequences", that is, the condition that "only alignments in which a partial sequence to be subjected to comparison begins at the 3' terminal of one sequence and ends at the 3' terminal of the other sequence".

Local alignment may be performed by inserting a gap. The gap means insertion and/or deletion (indel) of a base.

In addition, in the local alignment, a case where bases are complementary to each other between base sequence pairs is regarded as a match and a case where bases are not complementary to each other therebetween is regarded as a mismatch.

Alignment is performed such that scores for each of the match, the mismatch, and the indel are given and the total score becomes a maximum. The score may be appropriately set. For example, a scoring system may be set as in the following Table 1. "-" in Table 1 represents a gap (insertion and/or deletion (indel)).

TABLE 1

|   | A  | T  | G  | C  | —  |
|---|----|----|----|----|----|
| A | −1 | +1 | −1 | −1 | −3 |
| T | +1 | −1 | −1 | −1 | −3 |
| G | −1 | −1 | −1 | +1 | −3 |
| C | −1 | −1 | +1 | −1 | −3 |
| — | −3 | −3 | −3 | −3 |    |

"—": gap (indel)

For example, it is considered that local alignment is performed on base sequences of SEQ ID No: 1 and SEQ ID No: 2 shown in the following Table 2. Here, the scoring system is as shown in Table 1.

TABLE 2

| Base sequence (5' → 3') |
|---|
| SEQ ID No: 1: CGCTCTTCCGATCTCTGGCTTGGCCTTGGGAAT GTGG |
| SEO ID No: 2: CGCTCTTCCGATCTGACGGCAATATGGCCAATG ATGG |

Figure 2:
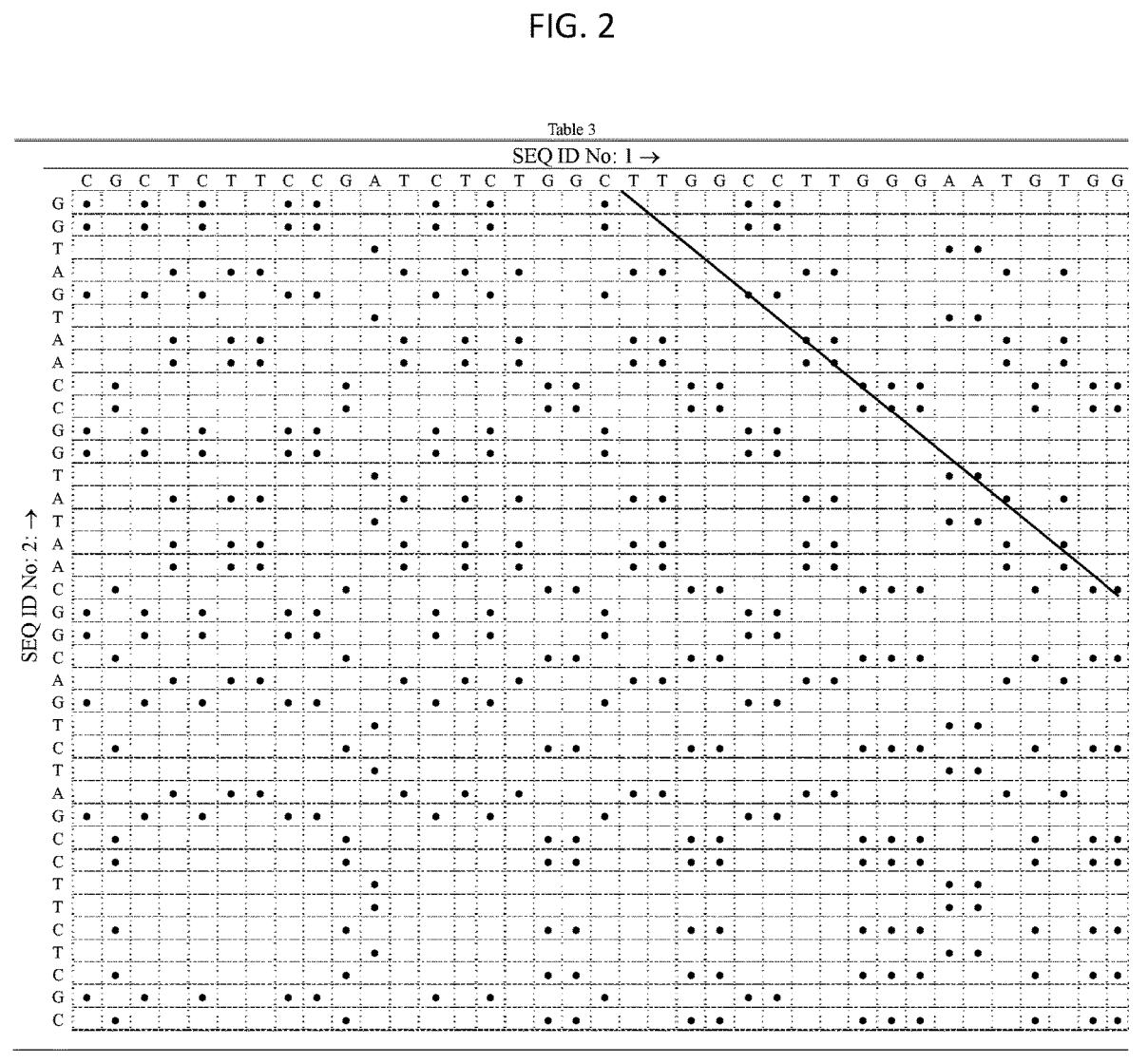

From the base sequences of SEQ ID No: 1 and SEQ ID No: 2, a dot matrix shown in FIG. 2 is generated. Specifically, the base sequence of SEQ ID No: 1 is arranged from the left to the right in an orientation of 5' to 3' and the base sequence of SEQ ID No: 2 is arranged from the bottom to the top in an orientation of 5' to 3'. "•" is filled in a grid of which bases are complementary to each other, and a dot matrix shown in FIG. 2 is obtained.

From the dot matrix shown in FIG. 2, Alignment (pairwise alignment) of partial sequences shown in the following Table 4 is obtained (refer to a diagonal line portion of FIG. 2).

Due to match (+1)×9, mismatch (−1)×9, and indel (−3)×0, the local alignment score is "±0".

The alignment (pairwise alignment) can be obtained not only through the dot matrix method exemplified herein, but also through a dynamic programming method, a word method, or various other methods.

(d) First Stage Selection Step

The first stage selection step is shown in the block diagram of FIG. 1 as "(FIRST) STEP OF FIRST STAGE SELECTION".

The first stage selection step is a step of performing first stage selection of base sequences of primer candidates which have been generated in the (b) Primer Candidate Base Sequence Generation Step, based on the local alignment score obtained in the above-described (c) Local Alignment Step.

A threshold value (first threshold value) of the local alignment score is predetermined.

In a case where a local alignment score of a pair of two base sequences is less than the first threshold value, it is determined that the pair of these two base sequences has low dimer formability, and the following step is performed. In contrast, in a case where a local alignment score of a pair of two base sequences is greater than or equal to the first threshold value, it is determined that the pair of these two base sequences has high dimer formability, and the following step is not performed on the pair.

The first threshold value is not particularly limited and can be appropriately set. For example, the first threshold value may be set using a PCR condition such as the amount of genomic DNA which becomes a template for a polymerase chain reaction.

Here, in the example in which the above-described (c) Local Alignment Step is shown, a case where the first threshold value is set to "3" is considered.

In the above-described example, the local alignment score is "±0" and is less than "3" which is the first threshold value. Therefore, it is possible to determine that the pair of the base sequences of SEQ ID No: 1 and SEQ ID No: 2 has low dimer formability.

The present step is performed on all of the pairs for which scores are calculated in the above-described (c) Local Alignment Step.

(e) Global Alignment Step

The global alignment step is shown in the block diagram of FIG. 1 as "(FIRST) GLOBAL ALIGNMENT STEP".

The global alignment step is a step of obtaining a global alignment score by performing pairwise global alignment on a base sequence which has a predetermined sequence length and includes the 3' terminal of the base sequence of the primer candidate regarding all pairs each consisting of two base sequences extracted from the base sequences of the primer candidates which have been generated in the above-described (b) Primer Candidate Base Sequence Generation Step and is used for amplifying a target region.

A combination of pairs of base sequences to be subjected to global alignment may be a combination selected while allowing overlapping, or may be a combination selected without allowing overlapping. However, in a case where formability of a primer dimer between primers of an iden-

TABLE 4

```
Partial sequence from SEQ ID No: 1:5'- T T G G C C T T G G G A A T G T G G -3'
                                          |     | | | |       | |   |     |
Partial sequence from SEQ ID No: 2:3'- G G T A G T A A C C G G T A T A A C -5'
``` tical base sequence has not yet been evaluated, the combination selected while allowing overlapping is preferable.

The total number of combinations is "$_mH_2=_{m+1}C_2=(m+1)!/2(m-1)!$" in a case where the selection is performed while allowing overlapping, and is "$_mC_2=m(m-1)/2$" in a case where the selection is performed without allowing overlapping, in which the number of base sequences which have been generated in the above-described (b) Primer Candidate Base Sequence Generation Step is set to be m.

In a case where both steps of (c) Local Alignment Step and (d) First Stage Selection Step which have been described above are performed first, the present step and (f) Second Stage Selection Step to be described below may be performed on primer candidates selected in (d) First Stage Selection Step.

Global alignment is an alignment which is performed on the entire sequence and in which it is possible to check complementarity of the entire sequence.

However, here, the "entire sequence" refers to the entirety of a base sequence which has a predetermined sequence length and includes the 3' terminal of a base sequence of a primer candidate.

Global alignment may be performed by inserting a gap. The gap means insertion and/or deletion (indel) of a base.

In addition, in the global alignment, a case where bases are complementary to each other between base sequence pairs is regarded as a match and a case where bases are not complementary to each other therebetween is regarded as a mismatch.

Alignment is performed such that scores for each of the match, the mismatch, and the indel are given and the total score becomes a maximum. The score may be appropriately set. For example, a scoring system may be set as in Table 1 described above. "-" in Table 1 represents a gap (insertion and/or deletion (indel)).

For example, it is considered that global alignment is performed on three bases (refer to portions with capital letters and correspond to the "base sequence which has a predetermined sequence length and includes the 3' terminal") at the 3' terminal of each base sequence of SEQ ID No: 1 and SEQ ID No: 2 shown in the following Table 5. Here, the scoring system is as shown in Table 1.

TABLE 5

| | Base sequence (5' → 3') |
|---|---|
| SEQ ID No: 1: | cgctcttccgatctctggcttggccttgggaat gTGG |
| SEQ ID No: 2: | cgctcttccgatctgacggcaatatggccaatg aTGG |

In a case of performing global alignment on base sequences of the three bases (portion with capital letters) at the 3' terminal of the base sequence of SEQ ID No: 1 and the three bases (portion with capital letters) at the 3' terminal of SEQ ID No: 2 such that the score becomes a maximum, it is possible to obtain alignment (pairwise alignment) shown in the following Table 6.

TABLE 6

| Three bases at 3' terminal of SEQ ID No: 1: | 5'- | T | G | G | -3' |
| Three bases at 3' terminal of SEQ ID No: 2: | 3'- | G | G | T | -5' |

As match (+1)×0, mismatch (−1)×3, and indel (−3)×0, the global alignment score is "−3".

The alignment (pairwise alignment) can be obtained through the dot matrix method a dynamic programming method, a word method, or various other methods.

(f) Second Stage Selection Step

The second stage selection step is shown in the block diagram of FIG. 1 as "(FIRST) STEP OF SECOND STAGE SELECTION".

The second stage selection step is a step of performing second stage selection of base sequences of primer candidates which have been generated in the above-described (b) Primer Candidate Base Sequence Generation Step based on the global alignment score obtained in the above-described (e) global alignment step.

A threshold value (second threshold value) of the global alignment score is predetermined.

In a case where a global alignment score of a pair of two base sequences is less than the second threshold value, it is determined that the pair of these two base sequences has low dimer formability, and the following step is performed. In contrast, in a case where a global alignment score of a pair of two base sequences is greater than or equal to the second threshold value, it is determined that the pair of these two base sequences has high dimer formability, and the following step is not performed on the pair.

The second threshold value is not particularly limited and can be appropriately set. For example, the second threshold value may be set using a PCR condition such as the amount of genomic DNA which becomes a template for a polymerase chain reaction.

It is possible to set the global alignment score obtained by performing pairwise global alignment on a base sequence which has a predetermined number of bases and includes the 3' terminal of a base sequence of each primer to be less than the second threshold value by setting a base sequence with several bases from the 3' terminal of a primer as an identical base sequence.

Here, in the example in which the above-described (e) Global Alignment Step is shown, a case where the second threshold value is set to "3" is considered.

In the above-described example, the global alignment score is "−3" and is less than "3" which is the second threshold value. Therefore, it is possible to determine that the pair of the base sequences of SEQ ID No: 1 and SEQ ID No: 2 has low dimer formability.

The present step is performed on all of the pairs for which scores are calculated in the above-described (e) Global Alignment Step.

Both steps of the above-described (c) Local Alignment Step and the above-described (d) First Stage Selection Step may be performed before or after both steps of the above-described (e) Global Alignment Step and the above-described (f) Second Stage Selection Step, or may be performed in parallel with both steps of the above-described (e) Global Alignment Step and the above-described (f) Second Stage Selection Step.

In addition, in order to reduce the amount of calculation, it is preferable to perform both steps of the above-described (c) Local Alignment Step and the above-described (d) First Stage Selection Step in a combination which has passed the above-described (f) Second Stage Selection Step after first performing both steps of the above-described (e) Global Alignment Step and the above-described (f) Second Stage Selection Step. Particularly, as the number of target regions and the number of base sequences of primer candidates are increased, the effect of reducing the amount of calculation is increased, and it is possible to speed up the overall processing.

This is because the amount of calculation of a global alignment score is smaller than that of a local alignment score which is obtained by searching a partial sequence with high complementarity from the entire base sequence under the condition that the base sequence includes the 3' terminal and it is possible to speed up the processing since global alignment is performed on a base sequence with a short length called a "predetermined sequence length" in the above-described (e) Global Alignment Step. It is known that the global alignment is faster than the local alignment in a case of alignment with respect to a sequence having an identical length in a well-known algorithm.

(Amplification Sequence Length-Checking Step)

If desired, an amplification sequence length-checking step of calculating the distance between ends of base sequences of primer candidates for which it has been determined that formability of a primer dimer is low in the above-described (d) First Stage Selection Step and the above-described (f) Second Stage Selection Step, on genomic DNA or chromosomal DNA regarding pairs of the base sequences of the primer candidates, and determining whether the distance is within a predetermined range may be performed.

In a case where the distance between the ends of the base sequences is within the predetermined range, it is possible to determine that there is a high possibility that the pairs of the base sequences of the primer candidates can appropriately amplify a target region. The distance between the ends of the base sequences of the primer candidates is not particularly limited, and can be appropriately set in accordance with the PCR condition such as the type of enzyme (DNA polymerase). For example, the distance between the ends of the base sequences of the primer candidates can be set to be within various ranges such as a range of 100 to 200 bases (pair), a range of 120 to 180 bases (pair), a range of 140 to 180 bases (pair) a range of 140 to 160 bases (pair), and a range of 160 to 180 bases (pair).

(g) Primer Employment Step

The primer employment step is shown in the block diagram of FIG. 1 as "(FIRST) PRIMER EMPLOYMENT STEP".

The primer employment step is a step of employing a base sequence of a primer candidate which has been selected in both of the above-described (d) First Stage Selection Step and the above-described (f) Second Stage Selection Step, as a base sequence of a primer for amplifying the above-described target region.

That is, in the present step, a base sequence of a primer candidate, in which a local alignment score obtained by performing pairwise local alignment on a base sequence of each primer candidate under a condition that a partial sequence to be subjected to comparison includes the 3' terminal of the base sequence is less than the first threshold value, and a global alignment score obtained by performing pairwise global alignment on a base sequence which has a predetermined number of bases and includes the 3' terminal of the base sequence of each primer candidate is less than the second threshold value, is employed as a base sequence of a primer for amplifying a target region.

For example, it is considered that base sequences of SEQ ID No: 1 and SEQ ID No: 2 shown in Table 7 are employed as base sequences of primers for amplifying a target region.

TABLE 7

| | Base sequence (5' → 3') |
|---|---|
| SEQ ID No: 1: | CGCTCTTCCGATCTCTGGCTTGGCCTTGGGAAT GTGG |
| SEQ ID No: 2: | CGCTCTTCCGATCTGACGGCAATATGGCCAATG ATGG |

As already described, the local alignment score is "±0" and is less than "3" which is the first threshold value. Moreover, the global alignment score is "−3" and is less than "3" which is the second threshold value.

Accordingly, it is possible to employ the base sequence of the primer candidate represented by SEQ ID No: 1 and the base sequence of primer candidate represented by SEQ ID No: 2 as base sequences of primers for amplifying a target region.

A second embodiment of a method for designing a primer and a primer set according to the present invention includes the following steps: ($a_1$) a first target region selection step of selecting a first target region in which the primer set used for the polymerase chain reaction is designed, from an objective region for determining a genetic condition which is selected in the objective region selection step; ($b_1$) a first primer candidate base sequence generation step of generating at least one base sequence of a primer candidate for amplifying the above-described first target region based on each base sequence in vicinity regions at both ends of the above-described first target region on the genome; ($c_1$) a first local alignment step of obtaining a local alignment score by performing pairwise local alignment on the base sequence of the above-described primer candidate under a condition that a partial sequence to be subjected to comparison includes the 3' terminal of the base sequence of the above-described primer candidate; ($d_1$) a first step of first stage selection of performing first stage selection of the base sequence of the above-described primer candidate based on the local alignment score obtained in the above-described ($c_1$) first local alignment step; ($e_1$) a first global alignment step of obtaining a global alignment score by performing pairwise global alignment on a base sequence which has a predetermined sequence length and includes the 3' terminal of the base sequence of the above-described primer candidate; ($f_1$) a first step of second stage selection of performing second stage selection of the base sequence of the above-described primer candidate based on the global alignment score obtained in the above-described ($e_1$) first global alignment step; ($g_1$) a first primer employment step of employing the base sequence of the primer candidate which has been selected in both of the above-described ($d_1$) first step of first stage selection and the above-described ($f_1$) first step of second stage selection as a base sequence of a primer for amplifying the above-described first target region; ($a_n$) an n-th target region selection step of selecting an n-th target region in which the primer set used for the polymerase chain reaction is designed, from the objective region for determining the genetic condition which is selected in the objective region selection step; ($b_n$) an n-th primer candidate base sequence generation step of generating at least one base sequence of each primer candidate for amplifying the above-described n-th target region based on each base sequence in vicinity regions at both ends of the above-described n-th target region on the genome; ($c_n$) an n-th local alignment step of obtaining a local alignment score by performing pairwise local alignment on the base sequence of the primer candidate for amplifying the above-described n-th target region and the base sequence of the primer which has already been employed, under a condition that partial sequences to be subjected to comparison include the 3' terminal of the base sequence of the above-described primer candidate and the 3' terminal of the base sequence of the above-described primer which has already been employed; ($d_n$) an n-th step of first stage selection of performing first stage selection of the base sequence of the primer candidate for amplifying the above-described n-th target region based on the local alignment score obtained in the above-described ($c_n$) n-th local alignment step; ($e_n$) an n-th global alignment step of obtaining a global alignment score by performing pairwise global alignment on base sequences which have a predetermined sequence length and include the 3' terminal of the base sequence of the primer candidate for amplifying the above-described n-th target region and the 3' terminal of the base sequence of the primer which has already been employed; ($f_n$) an n-th step of second stage selection of performing second stage selection of the base sequence of the primer candidate for amplifying the above-described n-th target region based on the global alignment score obtained in the above-described ($e_n$) n-th global alignment step; and ($g_n$) an n-th primer employment step of employing the base sequence of the primer candidate which has been selected in both of the above-described ($d_n$) n-th step of first stage selection and the above-described ($f_n$) n-th step of second stage selection as a base sequence of a primer for amplifying the above-described n-th target region.

Here, n is an integer of 2 or more, and each step from the above-described ($a_n$) n-th target region selection step to the above-described ($g_n$) n-th primer employment step regarding all target regions is repeated until base sequences of primers for amplifying the target regions are employed and until n reaches a number of objective regions selected in the objective region selection step.

Here, both steps of the above-described ($c_1$) first local alignment step and the above-described ($d_1$) first step of first stage selection are performed before or after both steps of the above-described ($e_1$) first global alignment step and the above-described ($f_1$) first step of second stage selection, or performed in parallel with both steps of the above-described ($e_1$) first global alignment step and the above-described ($f_1$) first step of second stage selection, and both steps of the above-described ($c_n$) n-th local alignment step and the above-described ($d_n$) n-th step of first stage selection are performed before or after both steps of the above-described ($e_n$) n-th global alignment step and the above-described ($f_n$) n-th step of second stage selection, or performed in parallel with both steps of the above-described ($e_n$) n-th global alignment step and the above-described ($f_n$) n-th step of second stage selection.

Each step of the second embodiment of the method for designing a primer and a primer set in the present invention will be described in detail.

($a_1$) First Target Region Selection Step ($a_1$) First Target Region Selection Step is shown in the block diagram of FIG. 1 as "(FIRST) TARGET REGION SELECTION STEP".

($a_1$) First Target Region Selection Step is the same as the above-described "(a) Target Region Selection Step" of the first embodiment except that one objective region is selected as a first target region.

($b_1$) First Primer Candidate Base Sequence Generation Step ($b_1$) First Primer Candidate Base Sequence Generation Step is shown in the block diagram of FIG. 1 as "(FIRST) PRIMER CANDIDATE BASE SEQUENCE GENERATION STEP".

($b_1$) First Primer Candidate Base Sequence Generation Step is the same as "(b) Primer Candidate Base Sequence Generation Step" of the first embodiment of the designing method of the present invention except that a base sequence of a primer candidate for amplifying the first target region selected in the above-described ($a_1$) First Target Region Selection Step is generated.

(Specificity-Checking Step)

The specificity-checking step is the same as "Specificity-Checking Step" of the first embodiment of the designing method of the present invention. The present step is an arbitrary step, and may be performed or may not be performed.

($c_1$) First Local Alignment Step ($c_1$) First Local Alignment Step is shown in the block diagram of FIG. 1 as "(FIRST) LOCAL ALIGNMENT STEP".

($c_1$) First Local Alignment Step is the same as "(c) Local Alignment Step" of the first embodiment of the designing method of the present invention except that local alignment is performed on the base sequence of the primer candidate for amplifying the first target region generated in the above-described ($b_1$) First Primer Candidate Base Sequence Generation Step.

($d_1$) First Step of First Stage Selection ($d_1$) First Step of First Stage Selection is shown in the block diagram of FIG. 1 as "(FIRST) STEP OF FIRST STAGE SELECTION".

($d_1$) First Step of First Stage Selection is the same as "(d) First Stage Selection Step" of the first embodiment of the designing method of the present invention except that the selection is performed on the base sequence of the primer candidate for amplifying the first target region generated in the above-described ($b_1$) First Primer Candidate Base Sequence Generation Step based on the local alignment score obtained in the above-described ($c_1$) First Local Alignment Step.

($e_1$) First Global Alignment Step ($e_1$) First Global Alignment Step is shown in the block diagram of FIG. 1 as "(FIRST) GLOBAL ALIGNMENT STEP".

($e_1$) First Global Alignment Step is the same as "(e) Global Alignment Step" of the first embodiment of the designing method of the present invention except that global alignment is performed on the base sequence of the primer candidate for amplifying the first target region generated in the above-described ($b_1$) First Primer Candidate Base Sequence Generation Step.

($f_1$) First Step of Second Stage Selection ($f_1$) First Step of Second Stage Selection is shown in the block diagram of FIG. 1 as "(FIRST) STEP OF SECOND STAGE SELECTION".

($f_1$) First Step of Second Stage Selection is the same as "(f) Second Stage Selection Step" of the first embodiment of the designing method of the present invention except that the selection is performed on the base sequence of the primer candidate for amplifying the first target region generated in the above-described ($b_1$) First Primer Candidate Base Sequence Generation Step based on the global alignment score obtained in the above-described ($e_1$) First Global Alignment Step.

Similarly to the first embodiment of the designing method of the present invention, both steps of the above-described ($c_1$) First Local Alignment Step and the above-described ($d_1$) First Step of First Stage Selection may be performed before or after both steps of the above-described ($e_1$) First Global Alignment Step and the above-described ($f_1$) First Step of Second Stage Selection, or may be performed in parallel with both steps of the above-described ($e_1$) First Global Alignment Step and the above-described ($f_1$) First Step of Second Stage Selection.

In addition, in order to reduce the amount of calculation, it is preferable to perform both steps of the above-described ($c_1$) First Local Alignment Step and the above-described ($d_1$) First Step of First Stage Selection Step in a combination which has passed the above-described ($f_1$) First Step of Second Stage Selection after first performing both steps of the above-described ($e_1$) First Global Alignment Step and the above-described ($f_1$) First Step of Second Stage Selection. Particularly, as the number of target regions and the number of base sequences of primer candidates are increased, the effect of reducing the amount of calculation is increased, and it is possible to speed up the overall processing.

(Amplification Sequence Length-Checking Step)

Amplification Sequence Length-Checking Step is the same as "Amplification Sequence Length-Checking Step" in the first embodiment. The present step is an arbitrary step, and may be performed or may not be performed.

($g_1$) First Primer Employment Step ($g_1$) First Primer Employment Step is shown in the block diagram of FIG. 1 as "(FIRST) PRIMER EMPLOYMENT STEP".

($g_1$) First Primer Employment Step is the same as "(g) Primer Employment Step" of the first embodiment of the designing method of the present invention except that the base sequence of the primer candidate for amplifying the first target region generated in the above-described ($b_1$) First Primer Candidate Base Sequence Generation Step is employed.

In the second embodiment of the present invention, a primer for amplifying the first target region is designed, and then, a primer for amplifying an n-th (n is an integer of 2 or more) target region is designed.

($a_n$) n-th Target Region Selection Step ($a_n$) n-th Target Region Selection Step is shown in the block diagram of FIG. 1 as "n-th TARGET REGION SELECTION STEP".

($a_n$) n-th Target Region Selection Step is the same as the above-described "(a) Target Region Selection Step" of the first embodiment except that one objective region is selected as an n-th target region from objective regions in which no target region has been selected up to an (n-1)th target region selection step.

The selection of the n-th target region can be simultaneously performed with the selection of an (n-1)th target region, or can be performed after the selection of the (n-1)th target region. Here, n is an integer of 2 or more.

($b_n$) n-th Primer Candidate Base Sequence Generation Step ($b_n$) n-th Primer Candidate Base Sequence Generation Step is shown in the block diagram of FIG. 1 as "n-th PRIMER CANDIDATE BASE SEQUENCE GENERATION STEP".

($b_n$) n-th Primer Candidate Base Sequence Generation Step is the same as "(b) Primer Candidate Base Sequence Generation Step" of the first embodiment of the designing method of the present invention except that a base sequence of a primer candidate for amplifying an n-th target region selected in the above-described ($a_n$) n-th Target Region Selection Step is generated.

(Specificity-Checking Step)

Specificity-Checking Step is the same as "Specificity-Checking Step" of the first embodiment of the designing method of the present invention. The present step is an arbitrary step, and may be performed or may not be performed.

($c_n$) n-th Local Alignment Step ($c_n$) n-th Local Alignment Step is shown in the block diagram of FIG. 1 as "n-th LOCAL ALIGNMENT STEP".

($c_n$) n-th Local Alignment Step is the same as "(c) Local Alignment Step" of the first embodiment of the designing method of the present invention except that local alignment is performed on the base sequence of the primer candidate for amplifying the n-th target region generated in the above-described ($b_n$) n-th Primer Candidate Base Sequence Generation Step and base sequences of primers which have already been employed.

Here, all the base sequences of the primers which have already been employed are base sequences which have been employed as base sequences of primers for amplifying target regions from the first target region to the (n-1)th target region (the same applies hereinafter).

($d_n$) n-th Step of First Stage Selection ($d_n$) n-th Step of First Stage Selection is shown in the block diagram of FIG. 1 as "n-th STEP OF FIRST STAGE SELECTION".

($d_n$) n-th Step of First Stage Selection is the same as "(d) First Stage Selection Step" of the first embodiment of the designing method of the present invention except that the selection is performed on the base sequence of the primer candidate for amplifying the n-th target region generated in the above-described ($b_n$) n-th Primer Candidate Base Sequence Generation Step and the base sequences of the primers which have already been employed, based on the local alignment score obtained in the above-described ($c_n$) n-th Local Alignment Step.

($e_n$) n-th Global Alignment Step ($e_n$) n-th Global Alignment Step is shown in the block diagram of FIG. 1 as "n-th GLOBAL ALIGNMENT STEP".

($e_n$) n-th Global Alignment Step is the same as "(e) Global Alignment Step" of the first embodiment of the designing method of the present invention except that global alignment is performed on the base sequence of the primer candidate for amplifying the n-th target region generated in the above-described ($b_n$) n-th Primer Candidate Base Sequence Generation Step and the base sequences of the primers which have already been employed.

($f_n$) n-th Step of Second Stage Selection ($f_n$) n-th Step of Second Stage Selection is shown in the block diagram of FIG. 1 as "n-th Step of Second Stage Selection".

($f_n$) n-th Step of Second Stage Selection is the same as "(f) Second Stage Selection Step" of the first embodiment of the designing method of the present invention except that the selection is performed on the base sequence of the primer candidate for amplifying the n-th target region generated in the above-described ($b_n$) n-th Primer Candidate Base Sequence Generation Step based on the global alignment score obtained in the above-described ($e_n$) n-th Global Alignment Step and the base sequences of the primers which have already been employed.

Similarly to the first embodiment of the designing method of the present invention, both steps of the above-described ($c_n$) n-th Local Alignment Step and the above-described ($d_n$)

n-th Step of First Stage Selection may be performed before or after both steps of the above-described ($e_n$) n-th Global Alignment Step and the above-described ($f_n$) n-th Step of Second Stage Selection, or may be performed in parallel with both steps of the above-described ($e_n$) n-th Global Alignment Step and the above-described ($f_n$) n-th Step of Second Stage Selection.

In addition, in order to reduce the amount of calculation, it is preferable to perform both steps of the above-described ($c_n$) n-th Local Alignment Step and the above-described ($d_n$) n-th Step of First Stage Selection in a combination which has passed the above-described ($f_n$) n-th Step of Second Stage Selection after performing both steps of the above-described ($e_n$) n-th Global Alignment Step and the above-described ($f_n$) n-th Step of Second Stage Selection" first. Particularly, as the number of target regions and the number of base sequences of primer candidates are increased, the effect of reducing the amount of calculation is increased, and it is possible to speed up the overall processing.

(Amplification Sequence Length-Checking Step)

Amplification Sequence Length-Checking Step is the same as "Amplification Sequence Length-Checking Step" of the first embodiment of the designing method of the present invention. The present step is an arbitrary step, and may be performed or may not be performed.

($g_n$) n-th Primer Employment Step ($g_n$) n-th Primer Employment Step is shown in the block diagram of FIG. 1 as "n-th PRIMER EMPLOYMENT STEP".

($g_n$) n-th Primer Employment Step is the same as "(g) Primer Employment Step" of the first embodiment of the designing method of the present invention except that the base sequence of the primer candidate for amplifying the n-th target region generated in the above-described ($b_n$) n-th Primer Candidate Base Sequence Generation Step is employed.

Hereinafter, the present invention will be described in more detail using Examples, but is not limited to these Examples.

EXAMPLES

Example 1

<Objective Region Selection>

SNPs on chromosome 13, chromosome 18, chromosome 21, and X chromosome are shown in Table 8 and Y chromosome-specific regions are shown in Table 9.

TABLE 8

| SNP ID | Chromosome | Position | Allele |
|---|---|---|---|
| rs7981616 | 13 | chr13:25265103 | A/G |
| rs1408184 | 13 | chr13:46946157 | C/T |
| rs1801244 | 13 | chr13:52544805 | C/G |
| rs2296984 | 13 | chr13:99457431 | T/G |
| rs946837 | 13 | chr13:101287340 | C/G, T |
| rs2230233 | 18 | chr18:29104698 | C/T |
| rs7233515 | 18 | chr18:44585955 | G/A, T |
| rs4940019 | 18 | chr18:48333203 | C/G |
| rs3809971 | 18 | chr18:56204977 | C/T |
| rs3744877 | 18 | chr18:77894844 | G/A |
| rs2073370 | 21 | chr21:35260481 | T/C |
| rs1041439 | 21 | chr21:40571246 | A/G |
| rs3746887 | 21 | chr21:41032740 | T/C |
| rs220312 | 21 | chr21:43519032 | G/A |
| rs4148973 | 21 | chr21:44323590 | T/G |
| rs2379206 | X | chrX:6995315 | C/T |
| rs5934730 | X | chrX:9935526 | G/T |

TABLE 8-continued

| SNP ID | Chromosome | Position | Allele |
|---|---|---|---|
| rs2071311 | X | chrX:30261002 | A/G |
| rs1801187 | X | chrX:32380996 | C/T |
| rs2293948 | X | chrX:48418126 | A/G |

TABLE 9

| Chromosome | Start position | Finish position |
|---|---|---|
| Y | 3609387 | 3609547 |
| Y | 7697094 | 7697262 |
| Y | 6792987 | 6793128 |
| Y | 14640461 | 14640619 |
| Y | 22902850 | 22903029 |

<Single Cell Isolation>

(Acquisition of Peripheral Blood Sample)

10.5 mg of sodium salts of ethylenediaminetetraacetic acid (EDTA) was added to a 7 mL blood collecting tube as an anticoagulant, and then, 7 mL of peripheral blood was obtained within the blood collecting tube as volunteer blood after obtaining informed consent from a pregnant woman volunteer. Thereafter, the blood was diluted using physiological salt solution.

(Concentration of Nucleated Red Blood Cell)

A liquid with a density of 1.070 (g/cm$^3$) and a liquid with a density of 1.095 (g/c were prepared using PERCOLL LIQUID (manufactured by GE Healthcare Bioscience), 2 mL of a liquid with a density of 1.095 g/mL was added to the bottom portion of a centrifuge tube, and the centrifuge tube was cooled in a refrigerator for 30 minutes at 4° C.

Thereafter, the centrifuge tube was taken out from the refrigerator and 2 mL of a liquid with a density of 1.070 (g/cm$^3$) was made to slowly overlap the top of the liquid with a density of 1.095 (g/cm$^3$) so as not to disturb the interface.

Then, 11 mL of diluent of blood which had been collected above was slowly added to the top of the medium with a density of 1.070 (g/cm$^3$) in the centrifuge tube.

Thereafter, centrifugation was performed for 20 minutes at 2000 rpm.

The centrifuge tube was taken out and fractions which had been deposited between the liquid with a density of 1.070 (g/cm$^3$) and the liquid with a density of 1.095 (g/cm$^3$) were collected using a pipette.

A droplet of the fractions of blood which have been collected in this manner was spotted at one end of a slide glass substrate 1 while holding the slide glass substrate 1 using one hand. A slide glass substrate 2 was held by the other hand and one end of the slide glass substrate 2 was brought into contact with the slide glass substrate 1 at an angle of 30°. The contact surface of the slide glass substrate 2 which was brought into contact with the fractions of blood was then spread into the space surrounded by the two sheets of slide glass due to a capillary phenomenon.

Next, the slide glass substrate 2 was made to be slid in a direction of a region opposite to the region of the slide glass substrate 1, on which blood was placed, while maintaining the angle, and the slide glass substrate 1 was uniformly coated with blood. After the completion of coating, the slide glass substrate 1 was sufficiently dried through air blowing for one or more hours. This glass substrate was immersed in a MAY-Grunwald staining liquid for three minutes and was washed by being immersed in a phosphoric acid buffer solution. Thereafter, the glass substrate was immersed in a GIEMSA staining liquid, which was diluted with a phosphoric acid buffer solution to make a concentration of 3%, for 10 minutes.

Thereafter, a plurality of stained glass substrates were prepared by being dried after being washed with pure water.

(Identification of Nucleated Red Blood Cell Using information on Shape of Cell)

In order to sort out nucleated red blood cell candidates from the cells with which the top of the slide glass substrate was coated, a measurement system of an optical microscope provided with an electric XY stage, an objective lens, and a CCD camera, a control unit provided with an XY stage control unit and a Z-direction control unit, and a control unit portion including an image input unit, an image processing unit, and an XY position recording unit were prepared. Blood cells which had been prepared as described above and with which the top of the slide glass substrate was coated were placed on the XY stage and scanning was performed by performing focusing on the slide glass. An image which was obtained using an optical microscope was taken and nucleated red blood cells which were objective cells were searched through image analysis.

In the image analysis, cells which satisfied the two following conditions were detected and the XY position was recorded.

$$0.25 < N/C < 1.0 \quad (1)$$

$$0.65 < N/L^2 < 0.785 \quad (2)$$

Here, "N" represents the area of a nuclear region of a cell on which mage analysis is to be performed, "C" represents the area of cytoplasm of a cell on which image analysis is to be performed, and "L" represents the length of the major axis of a nucleus of a cell on which image analysis is to be performed. The length of the major axis of a nucleus of a cell is defined as a length of the major axis of an elliptical shape circumscribing a cell nucleus which has a complicated shape.

Nucleated red blood cells which satisfy Formulas (1) and (2) were selected from nucleated red blood cells existing on the slide glass substrate, and were regarded as nucleated red blood cell candidates of the next step.

(Sorting of Fetal Nucleated Red Blood Cell)

Analysis of spectral information was performed on the nucleated red blood cell candidates, which had been identified in the step of identifying nucleated red blood cells using information on the shape of cells, using a microspectrometer.

The nucleated red blood cell candidates on the slide glass substrate were specified, one cell among them was irradiated with monochromatic light in the vicinity of 415 nm, and the absorption coefficient 2 of the cell was measured.

Next, three white blood cells of which the shapes of nuclei in the vicinity of the cell did not satisfy Formula (2) were selected from cells closest to the nucleated red blood cell candidates. The absorption coefficient of each white blood cell was calculated in the same manner, and an average absorption coefficient was calculated.

The absorption coefficients of remaining cells of the nucleated red blood cell candidates on the slide glass substrate were also measured similarly to the above, and an average value of the absorption coefficients of three white blood cells in the vicinity of each cell was calculated. Cells of which the ratio of the absorption coefficient of a nucleated red blood cell candidate to the average absorption coefficient of the white blood cells becomes greater than or equal to 1 were extracted from these results. As a result, 8 cells of which the ratio was clearly greater than or equal to 1 were detected.

(Cell Collection)

The 8 cells determined as described above were collected using a micromanipulator.

<Genomic DNA Extraction>

Cytolysis was performed on the collected single cells using a Single Cell WGA kit (manufactured by New England Biolabs). Specifically, each of the single cells was mixed in 5 µL of Cell extraction buffer, 4.8 µL of Extraction Enzyme Dilution Buffer and 0.2 µL of Cell Extraction Enzyme were mixed with each other to make the total amount of the solution be 10 µL, the solution was incubated for 10 minutes at 75° C., and then, the solution was further incubated for 4 minutes at 95° C., in accordance with the description of "Sample Preparation Methods" and "Pre-Amplification Protocol" in an instruction attached to the kit. Accordingly, genomic DNA was prepared.

<Designing of Primer Set Used for Polymerase Chain Reaction>

(Preparation of Primer)

25 Target regions were selected from the regions on chromosome 13, chromosome 18, chromosome 21, an X chromosome, and a Y chromosome for the purpose of analyzing the origins of fetal cells and a numerical abnormality of chromosomes. Regarding each of the target regions, primer sets for amplifying the target regions were designed such that the sequence length became 20 bp, the Tm value was within a range of 56 to 64° C., and the size of a PCR amplification product was within a range of 140 to 180 base pairs. Among them, 25 primer sets of which the 3' terminal-fixed local alignment score among the primers became less than 3 and the global alignment score of 3' terminal 3 bases of the primers became 0 were selected (Table 10).

TABLE 10

| Primer | | | | Target region | | PCR amplification product | | |
|---|---|---|---|---|---|---|---|---|
| Name | Base sequence (5' → 3') | Size | SEQ ID No | Chromosome | SNP ID | Size bp | Start position | Finish position |
| 1F | cgctcttccgatctctgGCTTGGCCTTGGGAATGTGG | 37b | 1 | 13 | rs7981616 | 180 | 25264999 | 25265178 |
| 1R | cgctcttccgatctgacGGCAATATGGCCAATGATGG | 37b | 2 | | | | | |
| 2F | cgctcttccgatctctgCTGTCAGTCTCAGGATATGG | 37b | 3 | 13 | rs1408184 | 173 | 46946120 | 46946292 |
| 2R | cgctcttccgatctgacGATACCACAGACTCCGTTGG | 37b | 4 | | | | | |
| 3F | cgctcttccgatctctgACTGCTCTGGTTGATTGTGG | 37b | 5 | 13 | rs1801244 | 164 | 52544717 | 52544880 |
| 3F | cgctcttccgatctgacTGTTCTACTAACCCTCTTGG | 37b | 6 | | | | | |

TABLE 10-continued

| Primer | | | | Target region | | PCR amplification product | | |
|---|---|---|---|---|---|---|---|---|
| Name | Base sequence (5' → 3') | Size | SEQ ID No | Chromosome | SNP ID | Size bp | Start position | Finish position |
| 4F | cgctcttccgatctctgTTCCCGGTCTGCGTAAATGG | 37b | 7 | 13 | rs2296984 | 162 | 99457303 | 99457464 |
| 4R | cgctcttccgatctgacGGTCAACCCTAAGGATCTGG | 37b | 8 | | | | | |
| 5F | cgctcttccgatctctgTCATTCTGTTCATCAGCTGG | 37b | 9 | 13 | rs946837 | 160 | 101287239 | 101287398 |
| 5R | cgctcttccgatctgacTAACCTGTTCTTCCGAGTGG | 37b | 10 | | | | | |
| 6F | cgctcttccgatctctgTTTGCAGCTTGAAGGGATGG | 37b | 11 | 18 | rs2230233 | 161 | 29104659 | 29104819 |
| 6R | cgctcttccgatctgacGAGCATCTGTTTCTATGTGG | 37b | 12 | | | | | |
| 7F | cgctcttccgatctctgCATCGGACTTTGCTTGATGG | 37b | 13 | 18 | rs7233515 | 142 | 44585836 | 44585977 |
| 7R | cgctcttccgatctgacTATATGTAGGCCGAAGTTGG | 37b | 14 | | | | | |
| 8F | cgctcttccgatctctgGTGACGCTTTTTAGCACTGG | 37b | 15 | 18 | rs4940019 | 180 | 48333122 | 48333301 |
| 8R | cgctcttccgatctgacTCTTTAGAGGGAGAGATTGG | 37b | 16 | | | | | |
| 9F | cgctcttccgatctctgCCCAACAAGAGAATCTATGG | 37b | 17 | 18 | rs3809971 | 175 | 56204947 | 56205121 |
| 9R | cgctcttccgatctgacTGACTTCAGGGAGCCTGTGG | 37b | 18 | | | | | |
| 10F | cgctcttccgatctctgTCTGGGGTTCTTCCTACTGG | 37b | 19 | 18 | rs3744877 | 172 | 77894713 | 77894884 |
| 10R | cgctcttccgatctgacCTGAGGAGGAGACTGTCTGG | 37b | 20 | | | | | |
| 11F | cgctcttccgatctctgGCCTCGAAGAGAGGGAATGG | 37b | 21 | 21 | rs2073370 | 171 | 35260401 | 35260571 |
| 11R | cgctcttccgatctgacGACCACAATCTCTCCCGTGG | 37b | 22 | | | | | |
| 12F | cgctcttccgatctctgCTGGGCAGTGTGAGAACTGG | 37b | 23 | 21 | rs1041439 | 174 | 40571215 | 40571388 |
| 12R | cgctcttccgatctgacTCTGAAAGTGTCTGTTCTGG | 37b | 24 | | | | | |
| 13F | cgctcttccgatctctgCTCATCCCACAAACAGTTGG | 37b | 25 | 21 | rs3746887 | 167 | 41032678 | 41032844 |
| 13R | cgctcttccgatctgacTAATGTCCCCGTGTCGCTGG | 37b | 26 | | | | | |
| 14F | cgctcttccgatctctgAATAGCCAGTGCTGTTCTGG | 37b | 27 | 21 | rs220312 | 171 | 43518893 | 43519063 |
| 14R | cgctcttccgatctgacACCACGTAGTCACTGACTGG | 37b | 28 | | | | | |
| 15F | cgctcttccgatctctgTTCAGAAGCTCGTCAGGTGG | 37b | 29 | 21 | rs4148973 | 168 | 44323536 | 44323703 |
| 15R | cgctcttccgatctgacAAGGAATGAGAGGCCTCTGG | 37b | 30 | | | | | |
| 16F | cgctcttccgatctctgAGGAAGATGTCCGGGTCTGG | 37b | 31 | X | rs2379206 | 170 | 6995304 | 6995473 |
| 16R | cgctcttccgatctgacATCCACCTGCGGAAACATGG | 37b | 32 | | | | | |
| 17F | cgctcttccgatctctgCCCTTACCACCATAGGATGG | 37b | 33 | X | rs5934730 | 164 | 9935444 | 9935607 |
| 17R | cgctcttccgatctgacTTTGGTTGTGGTGCTGTTGG | 37b | 34 | | | | | |
| 18F | cgctcttccgatctctgCCCGTGAAGAGGAAATCTGG | 37b | 35 | X | rs2071311 | 172 | 30260896 | 30261067 |
| 18R | cgctcttccgatctgacCACAGGAATTGATAGCGTGG | 37b | 36 | | | | | |
| 19F | cgctcttccgatctctgAAATGGCTGCAAATCGATGG | 37b | 37 | X | rs1801187 | 175 | 32380928 | 32381102 |
| 19R | cgctcttccgatctgacGTCCTATCTCTTGCTCATGG | 37b | 38 | | | | | |
| 20F | cgctcttccgatctctgAGCAGCTCAAGAGCGAGTGG | 37b | 39 | X | rs2293948 | 179 | 48418093 | 48418271 |
| 20R | cgctcttccgatctgaggTGGGTAACGGCATAGGTGG | 37b | 40 | | | | | |
| 21F | cgctcttccgatctctgATACCAGTTACTGGCAATGG | 37b | 41 | Y | | 161 | 3609387 | 3609547 |
| 21R | cgctcttccgatctgacACACAGACAGCGAAAGATGG | 37b | 42 | | | | | |
| 22F | cgctcttccgatctctgGGCAGGTGTCAGGCTTATGG | 37b | 43 | Y | | 169 | 7697094 | 7697262 |
| 22R | cgctcttccgatctgacTGGTGGCCTGGTAAAAGTGG | 37b | 44 | | | | | |
| 23F | cgctcttccgatctctgTCAGTCACACATCAGTCTGG | 37b | 45 | Y | | 142 | 6792987 | 6793128 |
| 23R | cgctcttccgatctgacATACAGATCACTGGAAGTGG | 37b | 46 | | | | | |
| 24F | cgctcttccgatctctgCGAGTTCTTAATGAGCTTGG | 37b | 47 | Y | | 159 | 14640461 | 14640619 |
| 24R | cgctcttccgatctgacGCTCATTGTGTTCCATGTGG | 37b | 48 | | | | | |
| 25F | cgctcttccgatctctgACATTGAAGGTAGCGTTGG | 37b | 49 | Y | | 180 | 22902850 | 22903029 |
| 25R | cgctcttccgatctgacGAGAAATCGGAGTTCATTGG | 37b | 50 | | | | | |

(Confirmation of Amplification through Singleplex PCR)

In order to confirm that each of the prepared primer sets can amplify the target regions, confirmation of amplification was performed through singleplex PCR.

Specifically, 2 μL of prepared genomic DNA (0.5 ng/μL), 2 μL of a primer mix, 12.5 μL of a multiplex PCR mix 2, 0.125 μL of a multiplex PCR mix 1, and a proper amount of water were mixed with each other to prepare 25 μL of a final amount of a reaction solution. The above-described primer mix is a mix obtained by mixing primers forming one primer set such that the final concentration of each of the primers becomes 50 nM. The above-described multiplex PCR mix 1 and the above-described multiplex PCR mix 2 are reagents contained in MULTIPLEX PCR ASSAY KIT (manufactured by TAKARA BIO INC.).

After performing initial thermal denaturation for 60 seconds at 94° C. using each of the prepared reaction solutions, a thermal cycle of thermal denaturation performed for 30 seconds at 94° C., annealing performed for 90 seconds at 60° C., and an elongation reaction performed for 30 seconds at 72° C. was repeated 30 times to perform singleplex PCR.

A part of the reaction solution on which the singleplex PCR was performed was subjected to agarose gel electrophoresis to check whether or not amplification has been performed.

<Amplification Performed through Polymerase Chain Reaction>

Multiplex PCR was performed using 25 primer sets from which it was possible to confirm that amplification was performed through singleplex PCR.

Specifically, 2 μL of prepared genomic DNA (0.5 ng/μL), 2 μL of a mix of 25 sets of the primers, 12.5 μL of a multiplex PCR mix 2, 0.125 μL of a multiplex PCR mix 1, and a proper amount of water were mixed with each other to prepare 25 μL of a final amount of a reaction solution. The above-described mix of 25 sets of the primers is a mix obtained by mixing primers forming 25 types of primer sets, from which it was possible to confirm that amplification was performed through singleplex PCR, such that the final concentration of each of the primers becomes 50 nM. The above-described multiplex PCR mix 1 and the above-described multiplex PCR mix 2 are reagents contained in MULTIPLEX PCR ASSAY KIT (manufactured by TAKARA BIO INC.).

After performing initial thermal denaturation for 60 seconds at 94° C. using each of the prepared reaction solution, a thermal cycle of thermal denaturation performed for 30 seconds at 94° C., annealing performed for 90 seconds at 60° C., and an elongation reaction performed for 30 seconds at 72° C. was repeated 30 times to perform multiplex PCR.

(Purification of PCR Product)

The obtained multiplex PCR product was purified using AMPure XP Kit (manufactured by BECKMAN COULTER). 45 μL of AMPure XP was added to 25 μL of a reaction solution to bond the PCR reaction product to magnetic beads. Contaminants were removed by separating the magnetic beads by magnetic force of Magna Stand (manufactured by NIPPON Genetics Co., Ltd.). After performing washing with 70% ethanol, nucleic acids bonded to the magnetic beads were eluted using a TE (tris(tris(hydroxymethyl)aminomethane)-ethylenediaminetetraacetic acid (EDTA)) buffer solution.

(Addition of Index Sequence and Sequence for Bonding Flow Cell)

In order to perform sequencing reaction using Miseq (manufactured by Mumma, Inc.), an index sequence for identifying a sample, and P5 and P7 sequences for bonding a flow cell were added to both terminals of the multiplex PCR product. 1.25 μM of P5_F(D501) and 1.25 μM of P7_R(D701 to D705) (shown in Table 11) were used as primers, and a reaction solution was prepared by mixing a multiplex PCR product, a multiplex PCR mix 1, a multiplex PCR mix 2, and water with each other. After performing initial thermal denaturation for 3 seconds at 94° C., a thermal cycle of thermal denaturation performed for 30 seconds at 94° C., annealing performed for 60 seconds at 50° C., and an elongation reaction performed for 30 seconds at 72° C. was repeated 5 times and a thermal cycle of thermal denaturation performed for 45 seconds at 94° C., annealing performed for 60 seconds at 55° C., and an elongation reaction performed for 30 seconds at 72° C. was performed 11 times. The above-described multiplex PCR mix 1 and the above-described multiplex PCR mix 2 are reagents contained in MULTIPLEX PCR ASSAY KIT (manufactured by TAKARA BIO INC.).

TABLE 11

| Primer name | Base sequence (5' → 3') | Sequence number |
|---|---|---|
| D501-F | AATGATACGGCGACCACCGAGATCTACACTATAGCCTTCTTTCCCTACACGACGCTCTTCCGATCTCTG | 51 |
| D701-R | CAAGCAGAAGACGGCATACGAGATCGAGTAATGTGACTGGAGTTCAGACGTGTGCTCTTCCGATCTGAC | 52 |
| D702-R | CAAGCAGAAGACGGCATACGAGATTCTCCGGAGTGACTGGAGTTCAGACGTGTGCTCTTCCGATCTGAC | 53 |
| D703-R | CAAGCAGAAGACGGCATACGAGATAATGAGCGGTGACTGGAGTTCAGACGTGTGCTCTTCCGATCTGAC | 54 |
| D704-R | CAAGCAGAAGACGGCATACGAGATGGAATCTCGTGACTGGAGTTCAGACGTGTGCTCTTCCGATCTGAC | 55 |
| D705-R | CAAGCAGAAGACGGCATACGAGATTTCTGAATGTGACTGGAGTTCAGACGTGTGCTCTTCCGATCTGAC | 56 |
| D706-R | CAAGCAGAAGACGGCATACGAGATACGAATTCGTGACTGGAGTTCAGACGTGTGCTCTTCCGATCTGAC | 57 |

The obtained PCR product was purified using AMPure XP KIT, and quantitative determination was performed using KAPA LIBRARY QUANTIFICATION KIT (manufactured by NIPPON Genetics Co, Ltd.) in order to accurately perform quantitative determination of the amplification product.

<DNA Sequencing>

Analysis was performed such that multiplex PCR products derived from single cells were sequenced using MiSeq Reagent Kit v2 300 Cycle (manufactured by Illumina, Inc.), the obtained FastQ file was mapped to a human genome sequence (hg19) using Burrows-Wheeler Aligner (BWA), genetic polymorphism information was extracted using SAMtools, and the number of times of sequence reading of each detection region was calculated using BEDtools.

(Confirmation on whether or not Isolated Nucleated Red Blood Cell is Derived from Fetus)

It was possible to confirm that one cell out of 8 cells had different types of SNP information by comparing SNPs of chromosome 13, chromosome 18, and chromosome 21 of each of the PCR amplification products amplified from each cell. A cell which was expected to be a white blood cell in accordance with the shape of a nucleus was separately collected from the top of the slide glass, which was coated with blood, using a micromanipulator, and DNA was amplified in the same manner using the primers which had been used during the amplification of the 8 cells to check SNP. As a result, it was confirmed that SNP of the cell was coincident with SNPs of the 7 cells. From the above, it was confirmed that 1 cell was defined as a fetus-derived nucleated red blood cell and 7 cells were defined as mother-derived nucleated cells. In addition, it was confirmed that the fetus was a female fetus since it was impossible to obtain information of a Y chromosome.

(Measurement of Amount of Amplification product (Number of Times of Sequence Reading))

The amount of amplification product of a detection region of chromosome 21 of a nucleated red blood cell which was identified as being derived from a fetus and was discriminated through sequence analysis of a multiplex PCR amplification product was defined through sequencing the amplification product using Miseq (registered trademark, manufactured by Illumina, Inc.) which was a next generation sequencer. The amount of amplification products (number of times of sequence reading) of detection regions of chromosome 21 of nucleated cells which were identified as being derived from a mother were separately measured by performing sequencing of the amplification products using Miseq. The variation between cells was small as a result of comparing the amounts of these amplification products (number of times of sequence reading), and the proportions of the amounts of these two amplification products were calculated. As a result, it was assumed that the proportions were values close to 1:1.5 and fetus was with trisomy.

Comparative Example 1

In the multiplex PCR amplification step, primer pairs in which complementarity between primers is not considered were designed instead of primer pairs which were used in Example 1 and designed such that complementarity between primers is reduced, for comparison for checking the effect of calculating the complementarity. Designing of primers was performed at a chromosomal location or on a gene similarly to Example 1 such that each of the primers with 20 bp of which the Tm value was 56° C. to 64° C. and the PCR amplification base length was 140 to 180 base pairs was prepared using Primer 3 (http://www-genome.wi.mitedu/ftp/distribution/software/).

Sequence determination of the amplification products was performed in the same manner as in Example 1 except that multiplex PCR was performed using these primer pairs. As a result, a mapping rate was significantly decreased and distribution of the amount of amplification product between cells was large. The variation between the cells was large enough that numerical abnormality could not be determined clearly.

The present invention is a technique of analyzing a fetus-derived single cell. In the present invention, a genetic polymorphism site and a somatic mutation site which are already well-known can be included in a detection region, and therefore, it is possible to determine the genetic condition without being limited to detection of a genetic abnormality.

[Sequence List]
International Application W-5618PCT Method for Determining Genetic Condition of Fetus JP16060444 20160330-00130141251600634028 Normal 20160330151113201602010907480070_P1AP101_W-_11.app Based on International Patent Cooperation Treaty

What is claimed is:

1. A method for determining a genetic condition of a fetus, the method comprising:
an objective region selection step of selecting an objective region for determining the genetic condition, from regions on a human genome;
a single cell isolation step of isolating a single cell from a maternal blood sample;
a genomic DNA extraction step of extracting genomic DNA from the single cell;
an amplification step performed through a polymerase chain reaction in which the objective region is amplified through the polymerase chain reaction using a primer set designed so as to amplify the objective region through the polymerase chain reaction using the genomic DNA extracted from the single cell as a template; and
a DNA sequencing step of decoding a DNA base sequence of an amplification product of the objective region obtained through the polymerase chain reaction,
wherein the objective region selection step is performed before or after both steps of the single cell isolation step and the genomic DNA extraction step, or performed in parallel with both steps of the single cell isolation step and the genomic DNA extraction step,
wherein the primer set designed so as to amplify the objective region through the polymerase chain reaction is designed through a method for designing a primer set used for the polymerase chain reaction, the method for designing a primer set including
a target region selection step of selecting a target region in which the primer set used for the polymerase chain reaction is designed, from the objective region,
a primer candidate base sequence generation step of generating at least one base sequence of a primer candidate for amplifying the target region based on each base sequence in vicinity regions at both ends of the target region on the genome,
a local alignment step of obtaining a local alignment score by performing pairwise local alignment on the base sequence of the primer candidate under a condition that a partial sequence to be subjected to comparison includes the 3' terminal of the base sequence of the primer candidate,
a first stage selection step of performing first stage selection of the base sequence of the primer candidate based on the local alignment score obtained in the local alignment step,
a global alignment step of obtaining a global alignment score by performing pairwise global alignment on a base sequence which is of three base length and includes the 3' terminal of the base sequence of the primer candidate,
a second stage selection step of performing second stage selection of a base sequence of the primer candidate based on the global alignment score obtained in the global alignment step, and
a primer employment step of employing the base sequence of the primer candidate which has been selected in both of the first stage selection step and the second stage selection step as a base sequence of a primer for amplifying the target region, and
wherein both steps of the local alignment step and the first stage selection step are performed before or after both steps of the global alignment step and the second stage selection step, or performed in parallel with both steps of the global alignment step and the second stage selection step, and
wherein the genetic condition is a numerical abnormality of a chromosome of the fetus,
an objective region for determining the genetic condition on at least one of chromosome 13, chromosome 18, and chromosome 21 is selected from regions on a human genome in the objective region selection step, and
the DNA base sequence of the amplification product of the objective region obtained through the polymerase chain reaction is decoded, a ratio of number of times of sequence reading of mother-derived amplification product to number of times of sequence reading of fetus-derived amplification product is obtained, and it is determined that the fetus has the numerical abnormality of the chromosome in a case where the ratio is greater than or equal to a predetermined cutoff value, in the DNA sequencing step.

2. The method for determining a genetic condition of a fetus according to claim 1,
wherein the primer set designed so as to amplify the objective region through the polymerase chain reaction is designed through a method for designing a primer set used for the polymerase chain reaction, the method for designing a primer set including
a first target region selection step of selecting a first target region in which the primer set used for the polymerase chain reaction is designed, from the objective region,
a first primer candidate base sequence generation step of generating at least one base sequence of a primer candidate for amplifying the first target region based on each base sequence in vicinity regions at both ends of the first target region on the genome,
a first local alignment step of obtaining a local alignment score by performing pairwise local alignment on the base sequence of the primer candidate under a condition that a partial sequence to be subjected to comparison includes the 3' terminal of the base sequence of the primer candidate,
a first step of first stage selection of performing first stage selection of the base sequence of the primer candidate based on the local alignment score obtained in the first local alignment step,
a first global alignment step of obtaining a global alignment score by performing pairwise global alignment on a base sequence which is of three base length and includes the 3' terminal of the base sequence of the primer candidate,
a first step of second stage selection of performing second stage selection of the base sequence of the primer candidate based on the global alignment score obtained in the first global alignment step,
a first primer employment step of employing the base sequence of the primer candidate which has been selected in both of the first step of first stage selection and the first step of second stage selection as a base sequence of a primer for amplifying the first target region,
a second target region selection step of selecting a second target region in which the primer set used for the polymerase chain reaction is designed, from the objective region,
a second primer candidate base sequence generation step of generating at least one base sequence of each primer candidate for amplifying the second target region based on each base sequence in vicinity regions at both ends of the second target region on the genome,
a second local alignment step of obtaining a local alignment score by performing pairwise local alignment on the base sequence of the primer candidate for amplifying the second target region and the base sequence of the primer which has already been employed, under a condition that partial sequences to be subjected to comparison include the 3' terminal of the base sequence of the primer candidate and the 3' terminal of the base sequence of the primer which has already been employed,
a second step of first stage selection of performing first stage selection of the base sequence of the primer candidate for amplifying the second target region based on the local alignment score obtained in the second local alignment step,
a second global alignment step of obtaining a global alignment score by performing pairwise global alignment on base sequences which have a predetermined sequence length and include the 3' terminal of the base sequence of the primer candidate for amplifying the second target region and the 3' terminal of the base sequence of the primer which has already been employed,
a second step of second stage selection of performing second stage selection of the base sequence of the primer candidate for amplifying the second target region based on the global alignment score obtained in the second global alignment step, and
a second primer employment step of employing the base sequence of the primer candidate which has been selected in both of the second step of first stage selection and the second step of second stage selection as a base sequence of a primer for amplifying the second target region,
wherein both steps of the first local alignment step and the first step of first stage selection are performed before or after both steps of the first global alignment step and the first step of second stage selection, or performed in parallel with both steps of the first global alignment step and the first step of second stage selection,
wherein both steps of the second local alignment step and the second step of first stage selection are performed before or after both steps of the second global alignment step and the second step of second stage selection, or performed in parallel with both steps of the second global alignment step and the second step of second stage selection, and
wherein, in a case where there are three or more of the target regions, the steps from the second target region selection step to the second primer employment step are repeated with respect to all of the target regions until a base sequence of a primer for amplifying each target region is employed.

3. The method for determining a genetic condition of a fetus according to claim 1,
wherein in case that the genetic condition of the fetus is not determined in the DNA sequencing step, the steps at least from the single cell isolation step to the DNA sequencing step are repeated until the genetic condition of the fetus can be determined.

4. The method for determining a genetic condition of a fetus according to claim 2,
wherein in case that the genetic condition of the fetus is not determined in the DNA sequencing step, the steps at least from the single cell isolation step to the DNA sequencing step are repeated until the genetic condition of the fetus can be determined.

5. The method for determining a genetic condition of a fetus according to claim 2,
wherein the genetic condition is a numerical abnormality of a chromosome of the fetus,
an objective region for determining the genetic condition on at least one of chromosome 13, chromosome 18, and chromosome 21 is selected from regions on a human genome in the objective region selection step, and
the DNA base sequence of the amplification product of the objective region obtained through the polymerase chain reaction is decoded, a ratio of number of times of sequence reading of mother-derived amplification product to number of times of sequence reading of fetus-derived amplification product is obtained, and it is determined that the fetus has the numerical abnormality of the chromosome in a case where the ratio is greater than or equal to a predetermined cutoff value, in the DNA sequencing step.

6. The method for determining a genetic condition of a fetus according to claim 3,
wherein the genetic condition is a numerical abnormality of a chromosome of the fetus,
an objective region for determining the genetic condition on at least one of chromosome 13, chromosome 18, and chromosome 21 is selected from regions on a human genome in the objective region selection step, and
the DNA base sequence of the amplification product of the objective region obtained through the polymerase chain reaction is decoded, a ratio of number of times of sequence reading of mother-derived amplification product to number of times of sequence reading of fetus-derived amplification product is obtained, and it is determined that the fetus has the numerical abnormality of the chromosome in a case where the ratio is greater than or equal to a predetermined cutoff value, in the DNA sequencing step.

7. The method for determining a genetic condition of a fetus according to claim 4,
wherein the genetic condition is a numerical abnormality of a chromosome of the fetus,
an objective region for determining the genetic condition on at least one of chromosome 13, chromosome 18, and chromosome 21 is selected from regions on a human genome in the objective region selection step, and
the DNA base sequence of the amplification product of the objective region obtained through the polymerase chain reaction is decoded, a ratio of number of times of sequence reading of mother-derived amplification product to number of times of sequence reading of fetus-derived amplification product is obtained, and it is determined that the fetus has the numerical abnormality of the chromosome in a case where the ratio is greater than or equal to a predetermined cutoff value, in the DNA sequencing step.

8. The method for determining a genetic condition of a fetus according to claim 1, the method further comprising:
a magnetic bead purification step of purifying the amplification product of the objective region obtained through the polymerase chain reaction, using magnetic beads, between the amplification step performed through a polymerase chain reaction and the DNA sequencing step.

9. The method for determining a genetic condition of a fetus according to claim 2, the method further comprising:
a magnetic bead purification step of purifying the amplification product of the objective region obtained through the polymerase chain reaction, using magnetic beads, between the amplification step performed through a polymerase chain reaction and the DNA sequencing step.

10. The method for determining a genetic condition of a fetus according to claim 3, the method further comprising:
a magnetic bead purification step of purifying the amplification product of the objective region obtained through the polymerase chain reaction, using magnetic beads, between the amplification step performed through a polymerase chain reaction and the DNA sequencing step.

11. The method for determining a genetic condition of a fetus according to claim 4, the method further comprising:
a magnetic bead purification step of purifying the amplification product of the objective region obtained through the polymerase chain reaction, using magnetic beads, between the amplification step performed through a polymerase chain reaction and the DNA sequencing step.

12. The method for determining a genetic condition of a fetus according to claim 5, the method further comprising:
a magnetic bead purification step of purifying the amplification product of the objective region obtained through the polymerase chain reaction, using magnetic beads, between the amplification step performed through a polymerase chain reaction and the DNA sequencing step.

\* \* \* \* \*